(12) United States Patent
Ikeda et al.

(10) Patent No.: US 8,283,095 B2
(45) Date of Patent: Oct. 9, 2012

(54) THIOURETHANE COMPOUND AND PHOTOSENSITIVE RESIN COMPOSITION

(75) Inventors: Haruhiko Ikeda, Kawasaki (JP); Hideo Miyata, Kawasaki (JP); Yotaro Hattori, Kawasaki (JP); Katsumi Murofushi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 835 days.

(21) Appl. No.: 12/438,098

(22) PCT Filed: Aug. 14, 2007

(86) PCT No.: PCT/JP2007/065836
§ 371 (c)(1),
(2), (4) Date: Feb. 19, 2009

(87) PCT Pub. No.: WO2008/023603
PCT Pub. Date: Feb. 28, 2008

(65) Prior Publication Data
US 2010/0233596 A1    Sep. 16, 2010

(30) Foreign Application Priority Data
Aug. 23, 2006  (JP) ................................ 2006-226806

(51) Int. Cl.
C07C 333/04     (2006.01)
C07C 333/08     (2006.01)
G03F 7/027      (2006.01)
G03F 7/029      (2006.01)
G03C 1/73       (2006.01)

(52) U.S. Cl. .......... 430/7; 430/282.1; 558/233; 558/240
(58) Field of Classification Search .................. None
See application file for complete search history.

(56) References Cited

U.S. PATENT DOCUMENTS

| 4,559,382 A | 12/1985 | Martens et al. |
| 4,631,229 A * | 12/1986 | Martens et al. ............... 428/343 |
| 6,455,207 B1 | 9/2002 | Katoh et al. |
| 2005/0261421 A1 | 11/2005 | Schmitt et al. |

FOREIGN PATENT DOCUMENTS

| JP | 60-006714 A | 1/1985 |
| JP | 02-129174 A | 5/1990 |
| JP | 02-247205 A | 10/1990 |
| JP | 04-080213 A | 3/1992 |
| JP | 05-215995 A | 8/1993 |
| JP | 10-253815 A | 9/1998 |
| JP | 2000-249822 A | 9/2000 |
| JP | 2001-011109 A | 1/2001 |
| JP | 2004-258346 A | 9/2004 |
| JP | 2005-104842 A | 4/2005 |
| JP | 2006-504829 A | 2/2006 |
| JP | 2007-009035 A | 1/2007 |

* cited by examiner

*Primary Examiner* — Joseph K. McKane
*Assistant Examiner* — Alicia L Otton
(74) *Attorney, Agent, or Firm* — Sughrue Mion, PLLC

(57) ABSTRACT

It is an object of the present invention to provide a photopolymerization initiator composition having high sensitivity and excellent storage properties, a photosensitive composition containing the photopolymerization initiator composition, and a thiourethane compound preferable for the photopolymerization initiator composition. The thiourethane compound of the present invention has 2 to 6 units each of which contains a moiety represented by the following formula (i) and a moiety represented by the following formula (ii).

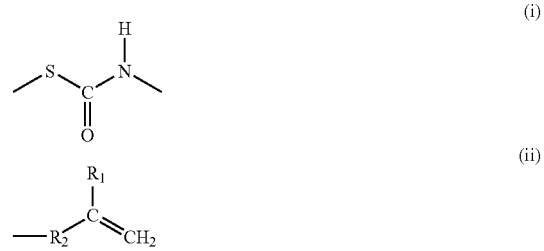

wherein $R_1$ is a hydrogen atom or a methyl group, and $R_2$ is —CO—, —COO— or —COOR$_3$— (wherein $R_3$ is an alkylene group of 2 to 6 carbon atoms).

13 Claims, 6 Drawing Sheets

THIOURETHANE COMPOUND AND PHOTOSENSITIVE RESIN COMPOSITION

CROSS REFERENCE TO RELATED APPLICATION

This application is a National Stage of International Application No. PCT/JP2007/065836 filed Aug. 14, 2007, claiming priority based on Japanese Patent Application No. 2006-226806, filed Aug. 23, 2006, the contents of all of which are incorporated herein by reference in their entirety.

TECHNICAL FIELD

The present invention relates to a thiourethane compound which is a block form of polyfunctional thiol preferable as a raw material for various coating materials, UV-curing or thermosetting coating materials, molding materials, adhesives, inks, optical materials, photo-shaping materials, printing board materials, resist materials, etc., and a photosensitive resin composition containing the thiourethane compound. More particularly, the invention relates to a curable composition whose ethylenically unsaturated double bond can be cured by heat or light with protecting a specific thiol compound by a thiourethane bond and which is excellent in stability.

BACKGROUND ART

In recent years, compositions which are cured by irradiation with active rays such as ultraviolet rays have been used in a wide variety of fields, such as fields of coating materials, UV-curing or thermosetting coating materials, molding materials, adhesives, inks, resists, optical materials, photo-shaping materials, printing board materials, dental materials, polymer cell materials and polymer raw materials. For example, they have been used for optical materials, such as coating materials for optical lenses and films, cladding materials for optical fibers, and optical adhesives for optical fibers or optical lenses.

As such curable compositions, compositions which are cured by lower energy, compositions which are cured more rapidly, compositions capable of forming more precise and finer patterns, compositions having deeper cure depth and compositions having higher storage properties have been desired according to the requirements of higher functions in the above-mentioned various fields of optical materials, electron materials, etc., and levels of requirements of various properties, e.g., optical properties such as transmittance and refractive index, adhesion to substrates and heat resistance, have become higher.

The photosensitive compositions are mainly constituted of a photopolymerization initiator, a compound having an ethylenically unsaturated bond which is cured by polymerization reaction, and various additives, and according to the use purpose, various kinds of components are employed. The photopolymerization initiator is selected based on its photosensitive wavelength or polymerization initiation properties, the compound having an ethylenically unsaturated bond and the additives are selected based on polymerizability or properties of a cured product desired, and they are used in combination.

As one of such photosensitive compositions, a curable composition containing a thiol compound is known. The curable composition of this kind is cured by irradiation with light in a short period of time of several seconds to several minutes after the compound containing a polyethylenically unsaturated double bond and the thiol compound undergo radical polymerization. Such a conventional polyene-polythiol-based photo-curing composition is excellent in processability and curability, but on the other hand, the composition has poor stability, and when the composition is kept in a liquid state before use, it is thickened and liable to suffer gelation. Moreover, there is a problem that a photo-cured product prepared from the composition having been kept in such a state has low heat resistance.

For example, when such a photosensitive composition containing straight-chain thiol as described in patent documents 1 and 2 is used as a photosensitive composition used for a color filter, the resulting photosensitive composition is sometimes improved in sensitivity but has insufficient storage stability, so that it is difficult to secure sufficient sensitivity when the composition is used.

In order to obtain a photosensitive composition having excellent storage stability with maintaining sensitivity of the photosensitive composition, the present inventors have paid attention to that selection of a photopolymerization initiator composition is important and particularly to that there is a problem in thermal reactivity of a thiol compound used as one component of the photopolymerization initiator composition.

Patent document 1: Japanese Patent Laid-Open Publication No. 253815/1998
Patent document 2: Japanese Patent Laid-Open Publication No. 249822/2000

DISCLOSURE OF THE INVENTION

Problem to be Solved by the Invention

It is an object of the present invention to provide a photopolymerization initiator composition having high sensitivity and excellent storage properties, a photosensitive composition containing the photopolymerization initiator composition, and a thiourethane compound which is novel and preferable for the photopolymerization initiator composition.

Means to Solve the Problem

The present inventors have earnestly studied in order to solve the above problems. As a result, they have found that the above problems can be solved by the use of a thiourethane compound obtained by allowing a thiol compound and an isocyanate compound to react with each other, and they have achieved the present invention.

The present invention relates to, for example, the following matters.

[1] A thiourethane compound having 2 to 6 units each of which contains a moiety represented by the following formula (i) and a moiety represented by the following formula (ii):

wherein $R_1$ is a hydrogen atom or a methyl group, and $R_2$ is —CO—, —COO— or —COOR$_3$— (wherein $R_3$ is an alkylene group of 2 to 6 carbon atoms).

[2] A thiourethane compound represented by the following formula (I):

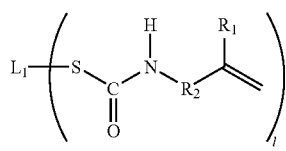

(I)

wherein $R_1$ is a hydrogen atom or a methyl group, $R_2$ is —CO—, —COO— or —COOR$_3$— (wherein $R_3$ is an alkylene group of 2 to 6 carbon atoms), l is an integer of 2 to 6, $L_1$ is an aliphatic substituent, an aromatic substituent, a heterocyclic ring-containing substituent or an alicyclic ring-containing substituent, and the substituent may contain an oxygen atom, a sulfur atom or a nitrogen atom.

[3] A thiourethane compound represented by the following formula (II):

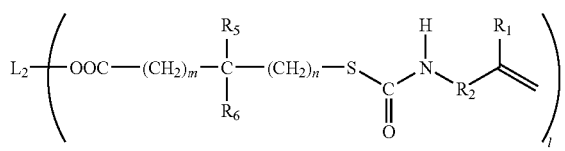

(II)

wherein $R_1$ is a hydrogen atom or a methyl group, $R_2$ is —CO—, —COO— or —COOR$_3$— (wherein $R_3$ is an alkylene group of 2 to 6 carbon atoms), $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[4] A thiourethane compound represented by the following formula (III):

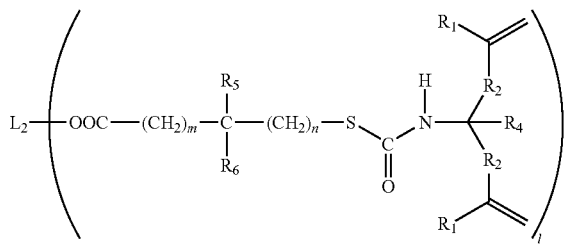

(III)

wherein $R_1$ is a hydrogen atom or a methyl group, $R_2$ is —CO—, —COO— or —COOR$_3$— (wherein $R_3$ is an alkylene group of 2 to 6 carbon atoms), $R_4$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[5] A thiourethane compound represented by the following formula (IV):

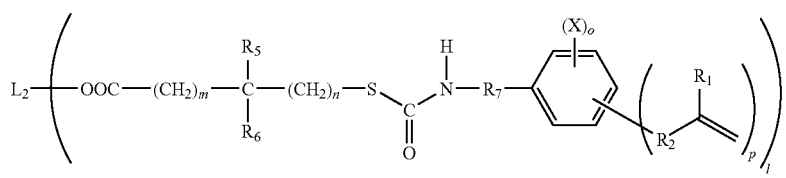

(IV)

wherein $R_1$ is a hydrogen atom or a methyl group, $R_2$ is —CO—, —COO— or —COOR$_3$— (wherein $R_3$ is an alkylene group of 2 to 6 carbon atoms), $R_5$ and $R_6$ are each a hydrogen atom or an alkyl group of 1 to 10 carbon atoms, $R_7$ is a direct bond or a straight-chain or branched alkylene group of 1 to 5 carbon atoms, m is 0 or an integer of 1 to 2, n is 0 or 1, l is an integer of 2 to 6, X is a hydrogen atom, a halogen atom or an electron attractive group, o is an integer of 0 to 4, p is an integer of 1 to 3, o and p satisfy the condition of $1 \leq o+p \leq 5$, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[6] A process for preparing the thiourethane compound of the above [3] which is represented by the formula (II), comprising allowing a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and an ethylenically unsaturated group-containing isocyanate compound represented by the following formula (VI) to react with each other;

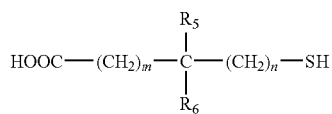

(V)

wherein $R_5$ and $R_6$ are each a hydrogen atom or an alkyl group of 1 to 10 carbon atoms, at least one of $R_5$ and $R_6$ is an alkyl group of 1 to 10 carbon atoms, m is 0 or an integer of 1 to 2, and n is 0 or 1;

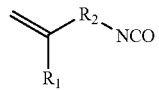

(VI)

wherein $R_1$ is a hydrogen atom or a methyl group, and $R_2$ is —CO—, —COO— or —COOR$_3$— (wherein $R_3$ is an alkylene group of 2 to 6 carbon atoms).

[7] A process for preparing the thiourethane compound of the above [4] which is represented by the formula (III), comprising allowing a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and an ethylenically unsaturated group-containing isocyanate compound represented by the following formula (VII) to react with each other;

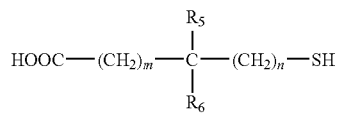

(V)

wherein $R_5$ and $R_6$ are each a hydrogen atom or an alkyl group of 1 to 10 carbon atoms, m is 0 or an integer of 1 to 2, and n is 0 or 1;

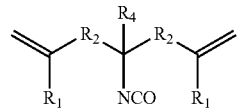

(VII)

wherein $R_1$ is a hydrogen atom or a methyl group, $R_2$ is —CO—, —COO— or —COOR$_3$— (wherein $R_3$ is an alkylene group of 2 to 6 carbon atoms), and $R_4$ is a hydrogen atom or a methyl group.

[8] A process for preparing the thiourethane compound of the above [5] which is represented by the formula (IV), comprising allowing a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and an ethylenically unsaturated group-containing isocyanate compound represented by the following formula (VIII) to react with each other;

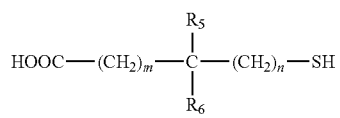

(V)

wherein $R_5$ and $R_6$ are each a hydrogen atom or an alkyl group of 1 to 10 carbon atoms, m is 0 or an integer of 1 to 2, and n is 0 or 1;

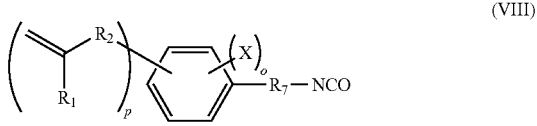

wherein $R_1$ is a hydrogen atom or a methyl group, $R_2$ is —CO—, —COO— or —COOR$_3$— (wherein $R_3$ is an alkylene group of 2 to 6 carbon atoms), $R_7$ is a direct bond or a straight-chain or branched alkylene group of 1 to 5 carbon atoms, X is a hydrogen atom, a halogen atom or an electron attractive group, is an integer of 0 to 4, p is an integer of 1 to 3, and o and p satisfy the condition of $1 \leq o+p \leq 5$.

[9] A thiourethane compound represented by the following formula (IX):

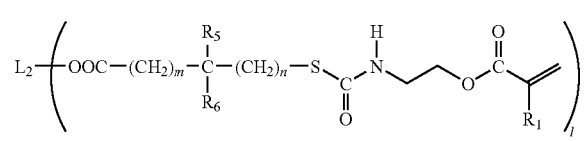

wherein $R_1$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[10] A thiourethane compound represented by the following formula (X):

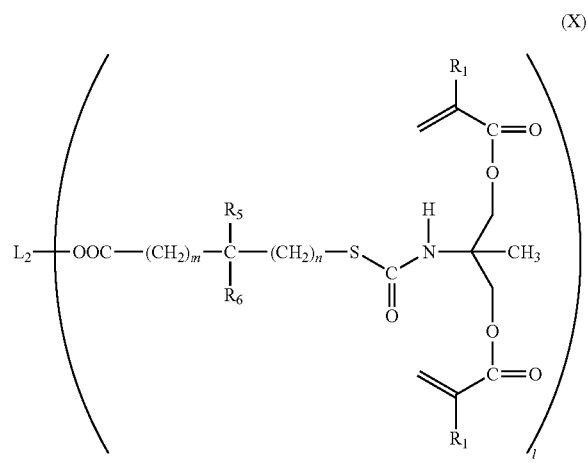

wherein $R_1$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[11] A thiourethane compound represented by the following formula (XI):

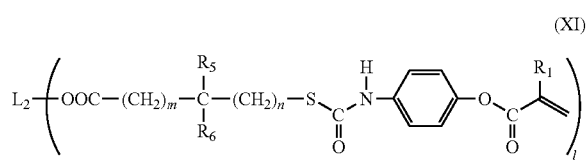

wherein $R_1$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[12] A thiourethane compound represented by the following formula (XII):

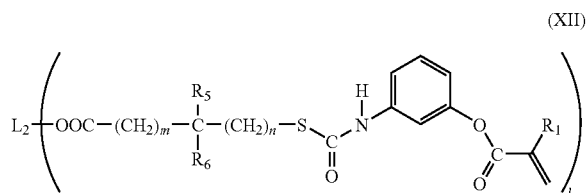

wherein $R_1$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent derived from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

[13] The process for preparing the thiourethane compound as stated in the above [6], wherein the temperature for the reaction of the thiol compound with the ethylenically unsaturated group-containing isocyanate compound represented by the formula (VI) is in the range of 0° C. to 70° C.

[14] The process for preparing the thiourethane compound as stated in the above [7], wherein the temperature for the reaction of the thiol compound with the ethylenically unsaturated group-containing isocyanate compound represented by the formula (VII) is in the range of 0° C. to 70° C.

[15] The process for preparing the thiourethane compound as stated in the above [8], wherein the temperature for the reaction of the thiol compound with the ethylenically unsaturated group-containing isocyanate compound represented by the formula (VIII) is in the range of 0° C. to 70° C.

[16] The process for preparing the thiourethane compound as stated in the above [6], wherein in the step of the reaction of the thiol compound with the ethylenically unsaturated group-containing isocyanate compound represented by the formula (VI), a catalyst is not used.

[17] The process for preparing the thiourethane compound as stated in the above [7], wherein in the step of the reaction of the thiol compound with the ethylenically unsaturated group-containing isocyanate compound represented by the formula (VII), a catalyst is not used.

[18] The process for preparing the thiourethane compound as stated in the above [8], wherein in the step of the reaction of the thiol compound with the ethylenically unsaturated group-containing isocyanate compound represented by the formula (VIII), a catalyst is not used.

[19] A photopolymerization initiator composition comprising the thiourethane compound of any one of the above [1] to [5] and [9] to [12] and a photopolymerization initiator.

[20] The photopolymerization initiator composition as stated in the above [19], wherein the photopolymerization initiator is at least one substance selected from α-hydroxyacetophenones, α-aminoacetophenones and biimidazoles.

[21] The photopolymerization initiator composition as stated in the above [19] or [20], further comprising a sensitizer.

[22] The photopolymerization initiator composition as stated in the above [21], wherein the sensitizer is at least one substance selected from benzophenones and anthraquinones.

[23] A photosensitive composition comprising the photopolymerization initiator composition of any one of the above [19] to [22] and a compound having an ethylenically unsaturated bond.

[24] The photosensitive composition as stated in the above [23], further comprising a high-molecular polymer.

[25] The photosensitive composition as stated in the above [24], wherein the high-molecular polymer is a polymer soluble in a solvent or an alkali aqueous solution.

[26] The photosensitive composition as stated in any one of the above [23] to [25], further comprising a pigment.

[27] A color filter having a colored pattern comprising the photosensitive composition of the above [26] on a substrate.

[28] A process for producing a color filter, having a step of forming a colored pattern comprising the photosensitive composition of the above [26] on a substrate.

Effect of the Invention

When a photopolymerization initiator composition containing the thiourethane compound of the present invention is used, a photosensitive composition, which has high sensitivity and therefore can shorten a production process and can reduce costs owing to enhancement of productivity, can be obtained.

The photosensitive composition of the present invention is favorably used in fields of resists for photoprocess, solder resists, etching resists, color filter resists, holograms, photo shaping, UV inks, etc., and it is particularly favorable for development type resists for forming precise and fine patterns.

BEST MODE FOR CARRYING OUT THE INVENTION

Figure 1:
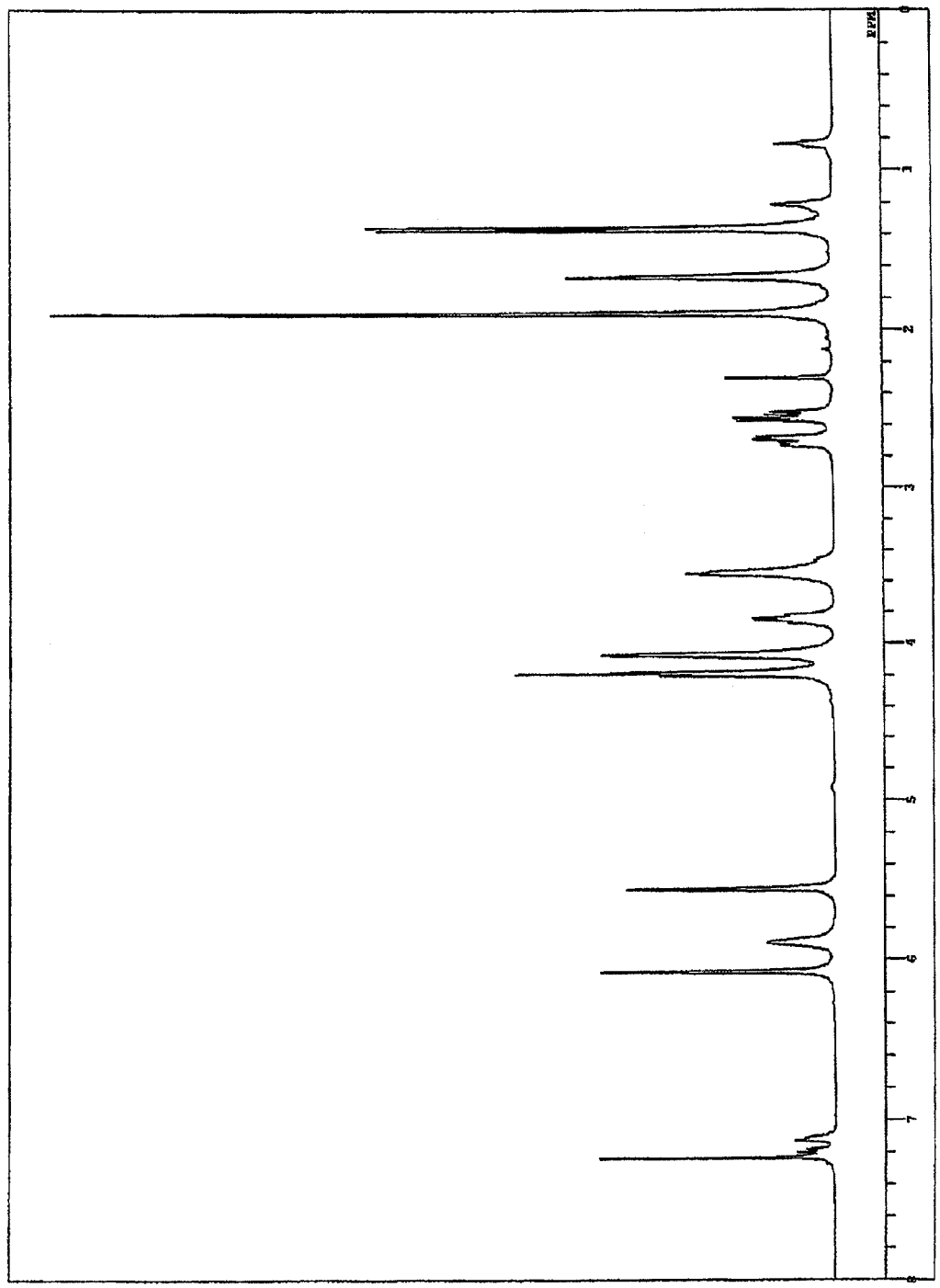
FIG. 1 is a graph of a $^1$H-NMR spectrum of a thiourethane compound BDMB-MOI synthesized in Thiourethane Compound Synthesis Example 1.

The thiourethane compound, the photopolymerization initiator composition containing the thiourethane compound and the photosensitive composition containing the photopolymerization initiator composition according to the invention are described in detail hereinafter.

1. Thiourethane Compound

The thiourethane compound of the invention is a compound having 2 to 6 units each of which contains a moiety represented by the formula (i) and a moiety represented by the formula (ii), and is more specifically a compound represented by the formula (I), preferably a compound represented by any one of the formulas (II) to (IV), more preferably a compound represented by any one of the formulas (IX) to (XII). Such a thiourethane compound of the invention can be obtained by, for example, thiourethanation reaction of a specific thiol compound with a specific ethylenically unsaturated group-containing isocyanate compound.

(1) Thiol Compound Having Mercapto Group-Containing Group

The thiol compound that is a precursor of the thiourethane compound of the invention is a thiol compound having a specific mercapto group-containing group, and the mercapto group-containing group is characterized by having a structure in which a carbon atom at the α-position and/or a carbon atom at the β-position to the mercapto group has a substituent. At least one of the substituents is preferably an alkyl group.

The structure in which a carbon atom at the α-position and/or a carbon atom the β-position to the mercapto group has a substituent means a structure in which the mercapto group is branched at carbon of the α-position and/or carbon of the β-position to the mercapto group, in other words, a structure in which carbon at the α-position and/or carbon at the β-position of the mercapto group is bonded to 3 or more atoms other than hydrogen, namely a branched structure. The case where at least one of the substituents is an alkyl group means that at least one of substituents other than the main chain at the α-position and/or the β-position to the mercapto group is an alkyl group. The main chain used herein indicates a structure of the longest chain containing a mercapto group and constituted of atoms other than hydrogen.

The mercapto group-containing group is particularly preferably a group represented by the following formula (XIII).

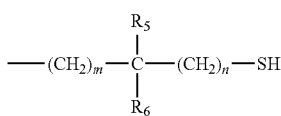

(XIII)

In the formula (XIII), $R_5$ and $R_6$ are each independently a hydrogen atom or an alkyl group of 1 to 10 carbon atoms. When $R_5$ and $R_6$ are both alkyl groups, they may the same or different.

The alkyl group of 1 to 10 carbon atoms indicated by $R_5$ and $R_6$ may be straight-chain or branched, and is, for example, a methyl group, an ethyl group, a n-propyl group, an isopropyl group, a n-butyl group, an isobutyl group, a tert-butyl group, a n-hexyl group or a n-octyl group, preferably a methyl group or an ethyl group.

m is 0 or an integer of 1 to 2, preferably 0 or 1, and n is 0 or 1, preferably 0.

The thiol compound for use in the invention is more preferably a polyfunctional thiol compound having two or more mercapto groups. Specifically, a polyfunctional thiol compound having two or more of the aforesaid mercapto group-containing groups is still more preferable. Because the thiol compound is polyfunctional as above, the thiol compound is characterized in that it can be made to have higher sensitivity with respect to photopolymerization and that crosslink density of the compound is increased, as compared with a monofunctional compound.

The thiol compound for use in the invention is more preferably a compound in which the mercapto group-containing group represented by the above formula (XIII) has a carboxylic acid derivative structure, as represented by the following formula (XIV).

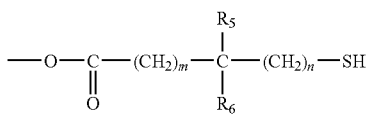

(XIV)

Further, such a thiol compound is preferably an ester of a mercapto group-containing carboxylic acid represented by the following formula (V) and an alcohol.

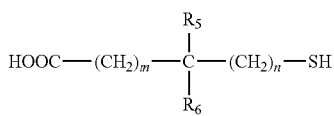

(V)

The alcohol is preferably a polyfunctional alcohol. By the use of the polyfunctional alcohol, a polyfunctional thiol compound can be obtained as the compound after the esterification reaction.

Examples of the polyfunctional alcohols include an alkylene glycol (the number of carbon atoms of the alkylene group is preferably 2 to 10, and the carbon chain thereof may be branched), diethylene glycol, glycerol, dipropylene glycol, trimethylolpropane, trimethylolethane, pentaerythritol and dipentaerythritol.

Examples of the alkylene glycols include ethylene glycol, trimethylene glycol, 1,2-propylene glycol, 1,2-butanediol, 1,3-butanediol, 2,3-butanediol and tetramethylene glycol.

Further, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate are also preferably employed.

Examples of the mercapto group-containing carboxylic acids represented by the formula (V) include 2-mercaptopropionic acid, 3-mercaptopropionic acid, 2-mercaptobutyric acid, 3-mercaptobutyric acid, 4-mercaptobutyric acid, 2-mercaptoisobutyric acid and 3-mercaptoisobutyric acid.

Specific examples of the thiol compounds having a structure represented by the formula (XIII) include the following compounds.

Examples of hydrocarbon dithiols include 2,5-hexanedithiol, 2,9-decanedithiol and 1,4-bis(1-mercaptoethyl)benzene.

Examples of compounds containing an ester linkage structure include phthalic acid di(1-mercaptoethyl ester), phthalic acid di(2-mercaptopropyl ester), phthalic acid di(3-mercaptobutyl ester) and phthalic acid di(3-mercaptoisobutyl ester).

Preferred examples include:

3-mercaptobutyrates, such as ethylene glycol bis(3-mercaptobutyrate), propylene glycol bis(3-mercaptobutyrate), diethylene glycol bis(3-mercaptobutyrate), butanediol bis(3-mercaptobutyrate), octanediol bis(3-mercaptobutyrate), trimethylolpropane tris(3-mercaptobutyrate), trimethylolethane tris(3-mercaptobutyrate), pentaerythritol tetrakis(3-mercaptobutyrate), dipentaerythritol hexakis(3-mercaptobutyrate), cyclohexanediol bis(3-mercaptobutyrate), cyclohexanedimethanol bis(3-mercaptobutyrate), norbornenedimethanol bis(3-mercaptobutyrate), bisphenol A bis(3-mercaptobutyrate), hydrogenated bisphenol A bis(3-mercaptobutyrate), 4,4'-(9-fluorenylidene)bis(2-phenoxyethanol)bis(3-mercaptobutyrate) and 2-hydroxyethanol triisocyanurate tris(3-mercaptobutyrate);

2-mercaptopropionates, such as ethylene glycol bis(2-mercaptopropionate), propylene glycol bis(2-mercaptopropionate), diethylene glycol bis(2-mercaptopropionate), butanediol bis(2-mercaptopropionate), octanediol bis(2-mercaptopropionate), trimethylolpropane tris(2-mercaptopropionate), trimethylolethane tris(2-mercaptopropionatee), pentaerythritol tetrakis(2-mercaptopropionate), dipentaerythritol hexakis(2-mercaptopropionate), cyclohexanediol bis(2-mercaptopropionate), cyclohexanedimethanol bis(2-mercaptopropionate), norbornenedimethanol bis(2-mercaptopropionate), bisphenol A bis(2-mercaptopropionate), hydrogenated bisphenol A bis(2-mercaptopropionate), 4,4'-(9-fluorenylidene)bis(2-phenoxyethanol)bis(2-mercaptopropionate) and 2-hydroxyethanol triisocyanurate tris(2-mercaptopropionate);

3-mercaptopropionates, such as ethylene glycol bis(3-mercaptopropionate), propylene glycol bis(3-mercaptopropionate), diethylene glycol bis(3-mercaptopropionate), butanediol bis(3-mercaptopropionate), octanediol bis(3-mercaptopropionate), trimethylolpropane tris(3-mercaptopropionate), trimethylolethane tris(3-mercaptopropionatee), pentaerythritol tetrakis(3-mercaptopropionate), dipentaerythritol hexakis(3-mercaptopropionate), cyclohexanediol bis(3-mercaptopropionate), cyclohexanedimethanol bis(3-mercaptopropionate), norbornenedimethanol bis(3-mercaptopropionate), bisphenol A bis(3-mercaptopropionate), hydrogenated bisphenol A bis(3-mercaptopropionate), 4,4'-(9-fluorenylidene)bis(2- phenoxyethanol)bis(3-mercaptopropionate) and 2-hydroxyethanol triisocyanurate tris(3-mercaptopropionate);

2-mercaptobutyrates, such as ethylene glycol bis(2-mercaptobutyrate), propylene glycol bis(2-mercaptobutyrate), diethylene glycol bis(2-mercaptobutyrate), butanediol bis(2-mercaptobutyrate), octanediol bis(2-mercaptobutyrate), trimethylolpropane tris(2-mercaptobutyrate), trimethylolethane tris(2-mercaptobutyrate), pentaerythritol tetrakis(2-mercaptobutyrate), dipentaerythritol hexakis(2-mercaptobutyrate), cyclohexanediol bis(2-mercaptobutyrate), cyclohexanedimethanol bis(2-mercaptobutyrate), norbornenedimethanol bis(2-mercaptobutyrate), bisphenol A bis(2-mercaptobutyrate), hydrogenated bisphenol A bis(2-mercaptobutyrate), 4,4'-(9-fluorenylidene)bis(2-phenoxyethanol)bis(2-mercaptobutyrate) and 2-hydroxyethanol triisocyanurate tris(2-mercaptobutyrate);

4-mercaptobutyrates, such as ethylene glycol bis(4-mercaptobutyrate), propylene glycol bis(4-mercaptobutyrate), diethylene glycol bis(4-mercaptobutyrate), butanediol bis(4-mercaptobutyrate), octanediol bis(4-mercaptobutyrate), trimethylolpropane tris(4-mercaptobutyrate), trimethylolethane tris(4-mercaptobutyrate), pentaerythritol tetrakis(4-mercaptobutyrate), dipentaerythritol hexakis(4-mercaptobutyrate), cyclohexanediol bis(4-mercaptobutyrate), cyclohexanedimethanol bis(4-mercaptobutyrate), norbornenedimethanol bis(4-mercaptobutyrate), bisphenol A bis(4-mercaptobutyrate), hydrogenated bisphenol A bis(4-mercaptobutyrate), 4,4'-(9-fluorenylidene)bis(2-phenoxyethanol)bis(4-mercaptobutyrate) and 2-hydroxyethanol triisocyanurate tris(4-mercaptobutyrate);

3-mercaptoisobutyrates, such as ethylene glycol bis(3-mercaptoisobutyrate), propylene glycol bis(3-mercaptoisobutyrate), diethylene glycol bis(3-mercaptoisobutyrate), butanediol bis(3-mercaptoisobutyrate), octanediol bis(3-mercaptoisobutyrate), trimethylolpropane tris(3-mercaptoisobutyrate), trimethylolethane tris(3-mercaptoisobutyrate), pentaerythritol tetrakis(3-mercaptoisobutyrate), dipentaerythritol hexakis(3-mercaptoisobutyrate), cyclohexanediol bis(3-mercaptoisobutyrate), cyclohexanedimethanol bis(3-mercaptoisobutyrate), norbornenedimethanol bis(3-mercaptoisobutyrate), bisphenol A bis(3-mercaptoisobutyrate), hydrogenated bisphenol A bis(3-mercaptoisobutyrate), 4,4'-(9-fluorenylidene)bis(2-phenoxyethanol)bis(3-mercaptoisobutyrate) and 2-hydroxyethanol triisocyanurate tris(3-mercaptoisobutyrate);

2-mercaptoisobutyrates, such as ethylene glycol bis(2-mercaptoisobutyrate), propylene glycol bis(2-mercaptoisobutyrate), diethylene glycol bis(2-mercaptoisobutyrate), butanediol bis(2-mercaptoisobutyrate), octanediol bis(2-mercaptoisobutyrate), trimethylolpropane tris(2-mercaptoisobutyrate), trimethylolethane tris(2-mercaptoisobutyrate), pentaerythritol tetrakis(2-mercaptoisobutyrate), dipentaerythritol hexakis(2-mercaptoisobutyrate), cyclohexanediol bis(2-mercaptoisobutyrate), cyclohexanedimethanol bis(2-mercaptoisobutyrate), norbornenedimethanol bis(2-mercaptoisobutyrate), bisphenol A bis(2-mercaptoisobutyrate), hydrogenated bisphenol A bis(2-mercaptoisobutyrate), 4,4'-(9-fluorenylidene)bis(2-phenoxyethanol)bis(2-mercaptoisobutyrate) and 2-hydroxyethanol triisocyanurate tris(2-mercaptoisobutyrate);

4-mercaptovalerates, such as ethylene glycol bis(4-mercaptovalerate), propylene glycol bis(4-mercaptovalerate), diethylene glycol bis(4-mercaptovalerate), butanediol bis(4-mercaptovalerate), octanediol bis(4-mercaptovalerate), trimethylolpropane tris(4-mercaptovalerate), trimethylolethane tris(4-mercaptovalerate), pentaerythritol tetrakis(4-mercaptovalerate), dipentaerythritol hexakis(4-mercaptovalerate), cyclohexanediol bis(4-mercaptovalerate), cyclohexanedimethanol bis(4-mercaptovalerate), norbornenedimethanol bis(4-mercaptovalerate), bisphenol A bis(4-mercaptovalerate), hydrogenated bisphenol A bis(4-mercaptovalerate), 4,4'-(9-fluorenylidene)bis(2-phenoxyethanol)bis(4-mercaptovalerate) and 2-hydroxyethanol triisocyanurate tris(4-mercaptovalerate); and 3-mercaptovalerates, such as ethylene glycol bis(3-mercaptovalerate), propylene glycol bis(3-mercaptovalerate), diethylene glycol bis(3-mercaptovalerate), butanediol bis(3-mercaptovalerate), octanediol bis(3-mercaptovalerate), trimethylolpropane tris(3-mercaptovalerate), trimethylolethane tris(3-mercaptovalerate), pentaerythritol tetrakis(3-mercaptovalerate), dipentaerythritol hexakis(3-mercaptovalerate), cyclohexanediol bis(3-mercaptovalerate), cyclohexanedimethanol bis(3-mercaptovalerate), norbornenedimethanol bis(3-mercaptovalerate), bisphenol A bis(3-mercaptovalerate), hydrogenated bisphenol A bis(3-mercaptovalerate), 4,4'-(9-fluorenylidene)bis(2-phenoxyethanol)bis(3-mercaptovalerate) and 2-hydroxyethanol triisocyanurate tris(3-mercaptovalerate).

Although the molecular weight of the above thiol compounds is not specifically restricted, it is in the range of preferably 200 to 1000.

The esters of mercapto group-containing carboxylic acids and alcohols can be obtained by allowing the aforesaid mercapto group-containing carboxylic acids represented by the formula (V) and the aforesaid alcohols to react with each other in accordance with a conventional process to form esters. The conditions for the esterification reaction are not specifically restricted, and they can be appropriately selected from the reaction conditions hitherto publicly known.

(2) Ethylenically Unsaturated Group-Containing Isocyanate

As the ethylenically unsaturated group-containing isocyanate compound that is a precursor of the thiourethane compound of the invention, a compound represented by the following formula (VI), (VII) or (VIII) (also referred to as a "compound (VI)", a "compound (VII)" or a "compound (VIII)" hereinafter) can be mentioned.

(VI)

wherein $R_1$ is a hydrogen atom or a methyl group, and $R_2$ is —CO—, —COO— or —COOR$_3$— (wherein $R_3$ is an alkylene group of 2 to 6 carbon atoms, preferably a straight-chain or branched alkylene group of 2 to 3 carbon atoms).

Preferred examples of the compounds (VI) include 2-acryloyloxyethyl isocyanate, 2-methacyloyloxyethyl isocyanate, 2-acryloyloxypropyl isocyanate, 2-methacryloyloxypropyl isocyanate, 2-acryloyloxybutyl isocyanate, 2-methacryloyloxybutyl isocyanate, 2-acryloyloxyisobutyl isocyanate, 2-methacryloyloxyisobutyl isocyanate, 2-acryloyloxyhexyl isocyanate and 2-methacryloyloxyhexyl isocyanate.

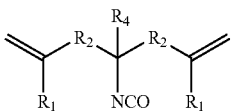

(VII)

wherein $R_1$ is a hydrogen atom or a methyl group, $R_2$ is —CO—, —COO— or —COOR$_3$— (wherein $R_3$ is an alkylene group of 2 to 6 carbon atoms, preferably a straight-chain or branched alkylene group of 2 to 3 carbon atoms), and $R_4$ is a hydrogen atom or a methyl group.

Preferred examples of the compounds (VII) include 1,3-acryloyloxypropane-2-isocyanate, 1,3-methacryloyloxypropane-2-isocyanate, 1,3-bisacryloyloxy-2-methylpropane-2-isocyanate, 1,3-bismethacryloyloxy-2-methylpropane-2-isocyanate, 1,2-bisacryloyloxypropane-1-isocyanate and 1,2-bismethacryloyloxypropane-1-isocyanate.

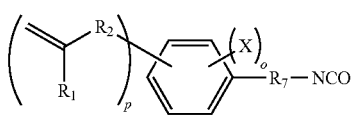

(VIII)

wherein $R_1$ is a hydrogen atom or a methyl group, $R_2$ is —CO—, COO— or —COOR$_3$— (wherein $R_3$ is an alkylene group of 2 to 6 carbon atoms, preferably a straight-chain or branched alkylene group of 2 to 3 carbon atoms), $R_7$ is a direct bond or a straight-chain or branched alkylene group of 1 to 5 carbon atoms, X is a hydrogen atom, a halogen atom or an electron attractive group, o is an integer of 0 to 4, p is an integer of 1 to 3, p is particularly preferably 1, and o and p satisfy the condition of $1 \leq o+p \leq 5$.

Preferred examples of the compounds (VIII) include 4-acryloyloxyphenyl isocyanate, 3-acryloyloxyphenyl isocyanate, 2-acryloyloxyphenyl isocyanate, 4-methacryloyloxyphenyl isocyanate, 3-(acryloyloxymethyl)phenyl isocyanate, 2-(acryloyloxymethyl)phenyl isocyanate, 3,5-bis(methacryloyloxyethyl)phenyl isocyanate and 2,4-bis(acryloyloxy)phenyl isocyanate.

(3) Process for Preparing Thiourethane Compound

The thiourethane compound of the invention can be prepared by thiourethanation reaction of the thiol compound with the ethylenically unsaturated group-containing isocyanate.

The reaction is carried out in the temperature range of usually 0° C. to 70° C. If the reaction temperature is not higher than 0° C., progress of the reaction is extremely slow. If the reaction temperature is not lower than 70° C., amounts of by-products or degrees of coloring increase, and in addition, reaction with the ethylenically unsaturated group (addition reaction called ene-thiol reaction) is liable to occur. Therefore, such temperatures are undesirable.

The reaction may be carried out after dilution with a solvent, when needed. Examples of the solvents employable include solvents other than those reactive to isocyanate, such as alcohols, carboxylic acids and amines. If water content is present in the system, reaction with isocyanate occurs, and therefore, a dehydrating solvent is preferably used.

In the thiourethanation reaction, a catalyst may be used, but if the reaction is completed without using a catalyst, use of no catalyst is preferable. In the case where a catalyst is used, the catalyst is not specifically restricted, but preferably used is organotin, such as tin octylate, dibutyltin dilaurate, dibutyltin acetate or dibutyltin dichloride, or organozinc, such as zinc octylate or zinc naphthenate. Such a catalyst can be added in an amount of 0.001 to 10 parts by weight based on 100 parts by weight of the thiol or the isocyanate.

2. Photopolymerization Initiator Composition and Photosensitive Composition Using the Same (1) Photopolymerization Initiator Composition The photopolymerization initiator composition of the invention comprises the aforesaid thiourethane compound and a photopolymerization initiator. The thiourethane compounds may be used singly or in combination of two or more kinds.

As the photopolymerization initiator, a general photopolymerization initiator is employable, and preferable are α-hydroxyacetophenones, α-aminoacetophenone and biimidazoles.

Examples of the α-hydroxyacetophenones include 2-hydroxy-2-methyl-1-phenylpropan-1-one, 2-hydroxy-2-methyl-1-phenylbutan-1-one, 1-(4-methylphenyl)-2-hydroxy-2-methylpropan-1-one, 1-(4-isopropylphenyl)-2-methylpropan-1-one, 1-(4-butylphenyl)-2-hydroxy-2-methylpropan-1-one, 2-hydroxy-2-methyl-1-(4-octylphenyl)propan-1-one, 1-(4-dodecylphenyl)-2-methylpropan-1-one, 1-(4-methoxyphenyl)-2-methylpropan-1-one, 1-(4-methylthiophenyl)-2-methylpropan-1-one, 1-(4-chlorophenyl)-2-hydroxy-2-methylpropan-1-one, 1-(4-bromophenyl)-2-hydroxy-2-methylpropan-1-one, 2-hydroxy-1-(4-hydroxyphenyl)-2-methylpropan-1-one, 1-(4-dimethylaminophenyl)-2-hydroxy-2-methylpropan-1-one, 1-(4-carboethoxyphenyl)-2-hydroxy-2-methylpropan-1-one, 1-hydroxycyclohexyl phenyl ketone and 2-hydroxy-1-(4-(2-hydroxyethoxy)-phenyl)-2-methylpropan-1-one.

Examples of the α-aminoacetophenones include 2-dimethylamino-2-methyl-1-phenylpropan-1-one, 2-diethylamino-2-methyl-1-phenylpropan-1-one, 2-methyl-2-morpholino-1-phenylpropan-1-one, 2-dimethylamino-2-methyl-1-(4-methylphenyl)propan-1-one, 2-dimethylamino-1-(4-ethylphenyl)-2-methylpropan-1-one, 2-dimethylamino-1-(4-isopropylphenyl)-2-methylpropan-1-one, 1-(4-butylphenyl)-2-dimethylamino-2-methylpropan-1-one, 2-dimethylamino-1-(4-methoxyphenyl)-2-methylpropan-1-one, 2-dimethylamino-2-methyl-1-[4-(methylthio)phenyl]propan-1-one, 2-methyl-1-[4-(methylthio)phenyl]-2-morpholino-propan-1-one, 2-benzyl-2-dimethylamino-1-(4-morpholinophenyl)-butan-1-one and 2-benzyl-2-dimethylamino-1-(4-dimethylaminophenyl)-butan-1-one.

Examples of the biimidazoles include 2,2'-bis(2-chlorophenyl)-4,4',5,5'-tetraphenyl-1,2'-biimidazole, 2,2'-bis(2-chlorophenyl)-4,4',5,5'-tetra(ethoxyphenyl)-1,2'-biimidazole, 2,2'-bis(2-chlorophenyl)-4,4',5,5'-tetra(4-bromophenyl)-1,2'-biimidazole, 2,2'-bis(2-chlorophenyl)-4,4',5,5'-tetra(4-methylphenyl)-1,2'-biimidazole, 2,2'-bis(2-chlorophenyl)-4,4',5,5'-tetra(4-ethylphenyl)-1,2'-biimidazole, 2,2'-bis(2-chlorophenyl)-4,4',5,5'-tetra(4-butylphenyl)-1,2'-biimidazole, 2,2'-bis(2-chlorophenyl)-4,4',5,5'-tetra(4-octylphenyl)-1,2'-biimidazole, 2,2'-bis(2-chlorophenyl)-4,4',5,5'-tetra(4-methoxyphenyl)-1,2'-biimidazole, 2,2'-bis(2-chlorophenyl)-4,4',5,5'-tetra(3-methoxyphenyl)-1,2'-biimidazole, 2,2'-bis(2,4-dichlorophenyl)-4,4',5,5'-tetraphenyl-1,2'-biimidazole, 2,2'-bis(2-fluorophenyl)-4,4',5,5'-tetra(3-methoxyphenyl)-1,2'-biimidazole, 2,2'-bis(2,6-difluorophenyl)-4,4',5,5'-tetra(3-methoxyphenyl)-1,2'-biimidazole and 2,2'-bis(2-methylphenyl)-4,4',5,5'-tetraphenyl-1,2'-biimidazole.

As other photopolymerization initiators, benzoin methyl ether, benzoin ethyl ether, benzoin isopropyl ether, benzyl methyl ketal, α-halogenoactophenones, methylphenyl glyoxylate, benzyl, anthraquinone, phenanthrenequinone, camphorquinone isophthalophenone, acylphosphine oxide, etc. are also employable.

The above photopolymerization initiators may be used singly or may be used in combination of two or more kinds.

In the photopolymerization initiator composition of the invention, the content of the thiourethane compound is in the range of preferably 10 to 90% by mass, and the content of the photopolymerization initiator is in the range of preferably 90 to 10% by mass.

In order to further increase sensitivity of the photopolymerization initiator composition of the invention, a sensitizer may be contained in the composition.

Examples of the sensitizers include cationic dyes, such as cyanine, xanthene, oxazine, thiazine, diarylmethane, triarylmethane and pyrylium; neutral dyes, such as melocyanine, coumarin, indigo, aromatic amine, phthalocyanine, azo, quinone and thioxanthene-based sensitizing dyes; and compounds, such as benzophenones, acetophenones, benzoins, thioxanthones, anthraquinones, imidazoles, biimidazoles, coumarins, ketocoumarins, triphenylpyryliums, triazines and benzoic acids. Further, compounds, such as acylphosphine oxide, methylphenyl glyoxylate, α-acyloxime ester, benzyl and camphorquinone, are also employable.

In the case of the cationic dyes, the counter anion is an arbitrary anion, and examples thereof include halogen ions, such as chlorine ion, bromine ion and iodine ion, benzenesulfonic acid anion, p-toluenesulfonic acid anion, methanesulfonic acid anion, $BF_4$ anion, $PF_6$ anion and perchloric acid anion.

Although the above sensitizers may be used singly or may be used in combination of two or more kinds, they should be determined taking into consideration a light emission pattern of the light source used.

Examples of the cationic dyes include Crystal Violet (C.I.42555), Methyl Violet (C.I.42535), Malachite Green (C.I.42000), fuchsine (C.I.42510), Crystal Violet-carbinol base (C.I.42555:1), parafuchsine (C.I.42500), Rhodamine B (C.I.45170), Victoria Blue B (C.I.44045), Victoria Pure Blue BOH(C.I.42595), Brilliant Green (C.I.42040), Night Blue BX (C.I.51185), Neutral Red (C.I.50040), Basic Yellow 1, 11, 13, 21, 28, 36, Basic Orange 21, 22, Basic Red 1 (C.I.45160), Basic Red 5 (C.I.50040), Basic Red 13 (C.I.48015), Basic Violet 7 (C.I.48020), Basic Violet 11 (C.I.45175), p-toluenesulfonic acid salt or naphthalenesulfonic acid salt of Crystal Violet, p-toluenesulfonic acid salt or perchloric acid salt of Victoria Blue B, p-toluenesulfonic acid salt or $BF_4$ salt of Basic Orange 21, and naphthalenesulfonic acid salt or $PF_6$ salt of Basic Red 5.

Examples of the electrically neutral dyes include 3-allyl-1-carboxymethyl-5-[2-(3-ethyl-2(3H)benzoxazolylidene)-2-thiohydantoin, 4-[2-(3-ethyl-2(3H)benzothiazolylidene)ethylidene]-3-phenyl-2-isoxazolin-5-one, 3-(2-benzothiazolyl)-7-(diethylamino)coumarin, 3-(2-benzimidazolyl)-7-(diethylamino)coumarin, ethyl 2,3,6,7-tetrahydro-1'-oxo-1H,5H,11H-[1]benzopyrano[6,7,8-ij]quinalizine-10-carboxylate, N,N'-diethylindigo, thioxoindigo, 2-dimethylaminoanthraquinone, 4-hydroxyazobenzene and 4-phenylamino-4'-nitroazobenzene.

Examples of other sensitizers include benzophenone, 4-methylbenzophenone, 4-dimethylaminobenzophenone, 4,4'-bis(dimethylamino)benzophenone, 4,4'-bis(diethylamino)benzophenone, 2,4-diethylthioxanthone, 2-methylthioxanthone, isopropylthioxanthone, anthraquinone, ethylanthraquinone, chloroanthraquinone, hydroxymethylanthraquinone, aminoanthraquinone, methylaminoanthraquinone, aceanthrenequinone, acenaphthenequinone, N-methylimidazole, coumarin, 7-diethylaminocoumarin and ethyl 4-dimethylaminobenzoate.

In the photopolymerization initiator composition of the invention, the amount of the sensitizer blended is in the range of preferably 5 to 50% by mass.

(2) Photosensitive Composition

The photosensitive composition of the invention contains the above-mentioned photopolymerization initiator composition and a compound having an ethylenically unsaturated bond, and it may further contain a high-molecular polymer, and it may furthermore contain various additives such as pigment and solvent, when needed.

With respect to photo curing due to radical polymerization, complete curing usually becomes difficult because polymerization is inhibited by oxygen in air at the interface between the composition and air. Therefore, in general, an air barrier layer such as a cover film is provided so that the surface should not come into contact with oxygen, or photo curing is carried out in an atmosphere of an inert gas such as argon gas or nitrogen. The photosensitive composition of the invention, however, exhibits sufficient curability irrespective of presence of oxygen, so that the composition can be favorably applied to uses in which use of no oxygen barrier layer is desirable, for example, the composition can be favorably used as a color filter-forming photosensitive composition.

By the use of the thiourethane compound of the invention in combination with the existing photopolymerization initiator in the photosensitive composition, maintenance of high sensitivity or enhancement of sensitivity and enhancement of storage stability can be made compatible with each other. In the case of conventional straight-chain type thiols (lauryl mercaptan, octanethiol, $HSCH_2CH_2COOH$ derivatives, etc.) and aromatic thiols such as mercapatobenzothiazole, enhancement of sensitivity can be achieved, but enhancement of storage stability cannot be achieved sufficiently.

The compound having an ethylenically unsaturated bond, which can be used in the photosensitive composition of the invention, is a compound generally called a monomer or an oligomer and is a compound capable of being cured by radical polymerization (or crosslinking) reaction. Examples of such compounds include (meth)acrylic acid, various (meth)acrylic acid esters, such as methyl(meth)acrylate, butyl (meth)acrylate, benzyl(meth)acrylate, 2-hydroxyethyl (meth)acrylate and 2-hydroxypropyl(meth)acrylate, ethylene glycol di(meth)acrylate, pentaerythritol tri(meth)acrylate, styrene, divinylbenzene, (meth)acrylamide, vinyl acetate, N-hydroxymethyl (meth) acrylamide, dipentaerythritol hexaacrylate, melamine acrylate and epoxyacrylate prepolymer. From the viewpoints of exposure sensitivity and various resistances after curing, a polyfunctional (meth)acrylic monomer is preferable. The above compounds having an ethylenically unsaturated bond may be used singly or may be used in combination of two or more kinds. The term "(meth)acryl" means both of "methacryl" and "acryl".

The high-molecular polymer employable for the photosensitive composition of the invention is a high-molecular polymer capable of forming a uniform film having a film thickness of not less than 1 μm. The high-molecular polymer is a transparent high-molecular polymer having a transmittance of preferably not less than 80%, more preferably not less than 95%, in all the wavelength region of 400 to 700 nm of the visible light region. The high-molecular polymer is preferably a polymer soluble in a developing solution (solvent or alkali aqueous solution).

As the high-molecular polymers, thermosetting resins, thermoplastic resins and photosensitive resins can be mentioned, and for example, polymers or copolymers, such as polyacrylates, poly-α-alkyl acrylates, polyamides, polyvinyl acetals, polyurethanes, polycarbonates, polystyrenes, polyvinyl esters, phenolic resin, epoxy resin, novolak resin and alkyd resin, can be used singly or as a mixture of two or more kinds.

For the purpose of accelerating curing reaction of the photosensitive composition of the invention or improving properties of a cured product, the high-molecular polymer may have an ethylenically unsaturated bond group capable of undergoing radical polymerization. In the case where the cured product is applied to uses in which it remains as a permanent film or endurance is required in the production process, e.g., a case where the cured product is used for a color filter, treatment at a high temperature and treatments with various solvents or chemicals are carried out in the post step in the production, so that it is preferable to use, as the high-molecular polymer, a polymer excellent in heat resistance and temporal stability.

Examples of the pigments include the following substances, which are all indicated by color index numbers. That is to say, there can be mentioned C.I. Pigment Yellow 12, 13, 14, 17, 20, 24, 55, 83, 86, 93, 109, 110, 117, 125, 137, 139, 147, 148, 153, 154, 166, 168; C.I. Pigment Orange 36, 43, 51, 55, 59, 61; C.I. Pigment Red 9, 97, 122, 123, 149, 168, 177, 180, 192, 215, 216, 217, 220, 223, 224, 226, 227, 228, 240; C.I. Pigment Violet 19, 23, 29, 30, 37, 40, 50; C.I. Pigment Blue 15, 15:1, 15:4, 15:6, 22, 60, 64; C.I. Pigment Green 7, 36; C.I. Pigment Brown 23, 25, 26; C.I. Pigment Black 7; and titanium black. These pigments may be used singly or may be used in combination of two or more kinds.

To the photosensitive composition of the invention, various additives can be added in order to impart viscosity, handling properties, cured product properties or the like according to the use purpose to the composition. For example, a volatile solvent may be added for the purpose of sufficiently dispersing the components, improving handling properties and adhesion properties in the coating, or adjusting viscosity.

Examples of the volatile solvents include alcohols, ketones and esters. More specifically, there can be mentioned methanol, ethanol, toluene, cyclohexane, isophorone, cellosolve acetate, diethylene glycol dimethyl ether, ethylene glycol diethyl ether, xylene, ethylbenzene, methyl cellosolve, ethyl cellosolve, butyl cellosolve, propylene glycol monomethyl ether, isoamyl acetate, ethyl lactate, methyl ethyl ketone, acetone, cyclohexanone, etc. These solvents may be used singly or may be used as a mixture of two or more kinds.

When use of the above volatile solvent is difficult because of the use purpose, a reactive solvent is employable. Examples of such solvents include 2-hydroxyethyl (meth) acrylate, methyl(meth)acrylate, n-butyl(meth)acrylate, cyclohexyl(meth)acrylate, isobornyl(meth)acrylate, N,N-dimethylaminoethyl (meth)acryalte, N-acryloylmorpholine, N-acryloylpiperidine, N,N-dimethyl(meth)acrylamide, N-vinylpyrrolidone and N-vinylacetamide. These solvents may be used singly or may be used as a mixture of two or more kinds, and if necessary, they may be mixed with the aforesaid volatile solvents.

The photosensitive composition of the invention may further contain fluorescent brightener, surface active agent, plasticizer, flame retardant, antioxidant, ultraviolet light absorber, blowing agent, mildewproofing agent, antistatic agent, magnetic material, conductive material, antibacterial/bactericidal material, porous adsorbent, perfume, etc. according to the purpose.

To the photosensitive composition of the invention, a thermal polymerization inhibitor may be added for the purpose of inhibiting polymerization during storage. Examples of the thermal polymerization inhibitors include p-methoxyphenol, hydroquinone, catechol, tert-butyl catechol, phenothiazine and methoquinone. For the purpose of preventing occurrence of gelation due to polymerization reaction or the like during dispersing, a polymerization inhibitor may be added. In order to favorably disperse a pigment, a dispersing agent may be appropriately added. The dispersing agent has an effect of helping dispersion of the pigment and an effect of preventing reaggregation after dispersing. For the purpose of obtaining appropriate flowability or obtaining light screening properties or mechanical/physical properties of the cured product, extender pigments, such as barium sulfate, calcium carbonate, silica, titania, alumina and aluminum powder, may be added.

Although the blending ratios of the components in the photosensitive composition of the invention are not determined indiscriminately, they are usually as follows.

When the compound having an ethylenically unsaturated bond and the high-molecular polymer are used in combination, the amount of the high-molecular polymer blended is in the range of generally 1 to 300 parts by mass, preferably 50 to 200 parts by mass, based on 100 parts by mass of the compound having an ethylenically unsaturated bond.

The amount of the photopolymerization initiator composition blended is in the range of generally 2 to 400 parts by mass, preferably 20 to 200 parts by mass, based on 100 parts by mass of the compound having an ethylenically unsaturated bond.

More specifically, it is preferable to blend the photopolymerization initiator composition in such an amount that the amount of the thiourethane compound in the photopolymerization initiator composition becomes generally 1 to 200 parts by mass, preferably 10 to 100 parts by mass, based on 100 parts by mass of the compound having an ethylenically unsaturated bond. If the amount of the thiourethane compound is too small, initiation of polymerization does not efficiently proceed occasionally, and even if the amount thereof is too large, improvement of the polymerization initiation function cannot be expected, and besides, evil influence is sometimes exerted on the properties of the cured product. Therefore, either case is undesirable.

Further, the photopolymerization initiator composition is desirably blended in such an amount that the amount of the sensitizer in the photopolymerization initiator composition becomes generally 1 to 60 parts by mass, preferably 2 to 30 parts by mass, based on 100 parts by mass of the compound having an ethylenically unsaturated bond. If the amount of the sensitizer is too small, sensitizing effect is not obtained occasionally. If the amount thereof is too large, light transmission efficiency is deteriorated because of light absorption by the sensitizer, and polymerization initiation efficiency is lowered. Therefore, either case is undesirable.

The amount of the pigment blended is in the range of generally about 100 to 2000 parts by mass based on 100 parts by mass of the compound having an ethylenically unsaturated bond.

The photosensitive composition of the invention can be prepared by mixing the above components by the use of various dispersing means, such as three-roll mill, two-roll mill, sand mill, attritor, ball mill, kneader and paint shaker. The monomer and the photopolymerization initiator may be blended after the pigment is dispersed.

(3) Method for Forming Pattern Using Photosensitive Composition

Next, a method for forming a pattern using the photosensitive composition of the invention is described.

First, the photosensitive composition of the invention is applied onto a substrate, e.g., glass, aluminum or polyester film such as polyethylene terephthalate (PET) film, by a coating method, such as spray coating, spinner coating, roll coating, screen coating, spread coating, dip coating or calender coating. For the purpose of obtaining appropriate coating properties, a small amount of a silicon-based or fluorine-based surface active agent may be added as a leveling agent or an anti-foaming agent.

After the photosensitive composition is applied, the volatile solvent is dried by a hot-air oven, a hot plate or the like under the conditions of generally 60 to 100° C. and 10 to 30 minutes, when needed. If the temperature is too high or the drying time is too long, partial polymerization or crosslinking takes place, and solubility of the unexposed part in the developing solution is lowered to sometimes cause so-called burning. Therefore, such a temperature or such a time is undesirable. The drying may be carried out under reduced pressure. Thereafter, an oxygen barrier film may be provided on the coating film depending upon the use purpose.

Subsequently, the dried coating film is exposed to light. In this case, ultraviolet light exposure may be carried out through a photomask having a pattern depending upon the use purpose. As the light source, an extra-high pressure mercury lamp, a metal halide lamp, a xenon lamp or the like is generally used, and depending upon the use purpose or the type of the substrate, a filter having hot-wire cutting property or wavelength selectivity may be used. After the light exposure, the unexposed part is removed, whereby a pattern can be formed on the substrate.

The methods for forming a pattern of a given shape using the photosensitive composition of the invention are broadly divided into two kinds of methods. One is a method wherein the photosensitive composition is applied in a desired shape and then cured by irradiation with light, and the other is a method wherein the photosensitive composition is uniformly applied onto a substrate and then cured by irradiation with light so that the exposed part may have a desired shape, and then the unexposed part is removed by means of washing, peeling, physical polishing, chemical polishing or the like to form a pattern from the residual photo-cured product.

The pattern formed from the photosensitive composition of the invention means a photo-cured product of the photosensitive composition that is formed on the substrate so as to keep a given shape, and is specifically a pattern for use in fields of resists for photoprocess, solder resists, etching resists, color filter resists, holograms, photo shaping, UV inks, etc. The photosensitive composition of the invention is particularly preferable for development type resists for forming precise and fine patterns.

Examples of the substrates employable in the above pattern formation include inorganic materials, such as glass and silicon, metallic materials, such as aluminum, stainless steel and copper, resin materials, such as PET, polyester, polyimide, epoxy resin, polyethylene and polycarbonate, and paper. The surface of such a substrate may be improved in adhesion to the photosensitive composition by oxidation treatment, acid treatment, plasma treatment, electrical discharge treatment or the like. The thickness of the substrate can be arbitrarily determined. Between the photosensitive composition and the substrate may be provided a resin layer or the like which does not participate in photo-reaction.

In the case where the uncured part of the photosensitive composition is removed by dissolution (development) after irradiation with light in the above-mentioned pattern-forming method, examples of solvents for the developing solution include organic solvents, such as N-methylpyrrolidone, methanol, ethanol, toluene, cyclohexane, isophorone, cellosolve acetate, diethylene glycol dimethyl ether, ethylene glycol diethyl ether, xylene, ethylbenzene, methyl cellosolve, ethyl cellosolve, butyl cellosolve, propylene glycol monomethyl ether, propylene glycol monomethyl ether acetate, isoamyl acetate, ethyl lactate, methyl ethyl ketone, acetone, cyclohexanone, N,N-dimethylformamide and acetonitrile; and alkali aqueous solutions. These solvents may be used singly or may be used in combination of two or more kinds. To these solvents, basic substances, such as trimethylamine and triethylamine, and surface active agents may be further added.

Examples of the alkali aqueous solutions employable include aqueous solutions of inorganic salts such as sodium hydroxide, potassium hydroxide, sodium carbonate and potassium carbonate; and aqueous solutions of organic salts such as hydroxytetramethylammonium and hydroxytetraethylammonium. These solutions may be also used singly or in combination of two or more kinds.

EXAMPLES

The present invention is further described with reference to the following examples, but it should be construed that the invention is in no way limited to those examples. In the following examples, the term "part(s)" means "part(s) by mass". The analytical equipments and the analytical conditions used in the examples are as follows.

Gas Chromatography (GC)

Analytical equipment: "GC14A" manufactured by Shimadzu Corporation

Column: "DB-1" manufactured by J & W Scientific Inc., 30 m×0.53 mm×1.5 µm

Column temperature: The temperature is raised up to 250° C. from 70° C. at 10° C./min and held at 250° C. for 18 minutes.

Integrator: "CR7A" manufactured by Shimadzu Corporation

Injection temperature: 220° C.

Detector temperature: 270° C., FID

Detector: FID, $H_2$ 40 ml/min, air 400 ml/min

Carrier gas: He 10 ml/min

High performance liquid chromatography (HPLC)

Column: "Shodex 5C84E" manufactured by Showa Denko K.K.

Composition of eluting solution: acetonitrile/water=3/1 (by volume), 2 mM tetra-n-butylammonium perchlorate Pump: "Shodex DS-4" manufactured by Showa Denko K.K.

Detector: "Shodex UV-41" manufactured by Showa Denko K.K., "Shodex RI-71" manufactured by Showa Denko K.K.

Detection wavelength: 210 nm

Thiol Synthesis Example 1

Synthesis of butanediol bis(3-mercaptobutyrate) (BDMB)

In a 300 ml egg plant type flask, 20 g (222 mmol) of butanediol (available from Wako Pure Chemical Industries, Ltd.), 58.7 g (488 mmol) of 3-mercaptobutanoic acid (available from Yodo Chemical Co., Ltd.), 2.78 g (14.6 mmol) of p-toluenesulfonic acid monohydrate (available from Junsei Chemical Co., Ltd.) and 100 g of toluene (available from Junsei Chemical Co., Ltd.) were placed, and a Dean-Stark device and a cooling tube were installed. The contents in the flask were heated at an oil bath temperature of 140° C. with stirring. After 4 hours from the initiation of reaction, the reaction solution was allowed to cool, washed with ion-exchanged water and then neutralized with a saturated sodium hydrogencarbonate aqueous solution. The resulting solution was further washed with ion-exchanged water three times and then subjected to dehydration-drying using anhydrous magnesium sulfate (available from Junsei Chemical Co., Ltd.). Next, toluene was distilled off, and the remainder was subjected to column chromatography by a silica gel to perform purification of BDMB. As the silica gel, Wako gel C-200 (available from Wako Pure Chemical Industries, Ltd.) was used, and as the elution solvent, n-hexane/acetone (7/1 by volume) was used. The BDMB obtained by purification was a colorless transparent liquid, and the yield was 31.1 g (48%).

Thiol Synthesis Example 2

Synthesis of trimethylolpropane tris(3-mercaptobutyrate) (TPMB)

TPMB was synthesized by the process described in Japanese Patent Laid-Open Publication No. 149755/2004.

Thiol Synthesis Example 3

Synthesis of pentaerythritol tetrakis(3-mercaptobutyrate) (PEMB)

In a 300 ml egg plant type flask, 26 g (102 mmol) of pentaerythritol (available from Tokyo Chemical Industry, Co., Ltd.), 54 g (450 mmol) of 3-mercaptobutanoic acid (available from Yodo Chemical Co., Ltd.), 2.6 g (13.5 mmol) of p-toluenesulfonic acid monohydrate (available from Junsei Chemical Co., Ltd.) and 100 g of toluene (available from Junsei Chemical Co., Ltd.) were placed, and a Dean-Stark device and a cooling tube were installed. The contents in the flask were heated at an oil bath temperature of 140° C. with stirring. After 4 hours from the initiation of reaction, the reaction solution was allowed to cool, washed with ion-exchanged water and then neutralized with a saturated sodium hydrogencarbonate aqueous solution. The resulting solution was further washed with ion-exchanged water three times and then subjected to dehydration-drying using anhydrous magnesium sulfate (available from Junsei Chemical Co., Ltd.). Next, toluene was distilled off, and the remainder was subjected to column chromatography by a silica gel to perform purification of PEMB. As the silica gel, Wako Gel C-200 (available from Wako Pure Chemical Industries, Ltd.) was used, and as the elution solvent, n-hexane/acetone (7/1 by volume) was used. The PEMB obtained by purification was a colorless transparent liquid, and the yield was 24.5 g (21%).

Isocyanate Synthesis Example 1

Synthesis of 1,3-bisacryloyloxy-2-methyl-propane-2-isocyanate (BEI)

(First Step)
In a 500 ml four-necked flask equipped with a stirrer, a thermometer, a dropping funnel and a reflux condenser, 20.0 g (0.19 mol) of 2-amino-2-methyl-1,3-propanediol and 200 ml of toluene were placed in a nitrogen atmosphere. Then, a hydrogen chloride gas was fed at a flow rate of 100 ml/min for 1 hour.

(Second Step)
The solution obtained in the first step was heated to 95° C., then 54.3 g (0.43 mol) of 3-chloropropionyl chloride was fed over a period of 1 hour, and heating was further continued at 95° C. for 1 hour.

(Third Step)
With maintaining the solution obtained in the second step at 90° C., 43.0 g (0.43 mol) of carbonyl chloride was fed over a period of 4 hours, and heating was further continued at 90° C. for 1 hour. Thereafter, carbonyl chloride dissolved in the reaction solution was removed by introducing nitrogen into the solution.

(Fourth Step)
The solution obtained in the third step had an alkali-decomposable substance concentration of 7.9%, and in 200 g of the solution, the amount of alkali-decomposable chlorine was 15.8 g (0.45 mol). The solution was placed in a 500 ml flask, and 0.05 g of phenothiazine and 0.05 g of 2,6-bis-t-butylhydroxytoluene were added as polymerization inhibitors. Thereafter, 45.0 g (0.45 mol) of triethylamine was dropwise added over a period of 1 hour. The temperature of the solution to which the dropwise addition had been initiated at 25° C. rose to 60° C. because of heat generation. The solution was heated to 70° C., then heating and stirring were continued for 5 hours, and thereafter the solution was cooled to room temperature. The resulting solid matters were separated by filtration and washed with toluene to obtain 200 g of a filtrate. As a result of analysis by gas chromatography, the amount of 1,3-bisacryloyloxy-2-methyl-propane-2-isocyanate obtained was 32.2 g (0.13 mol) (yield: 71%).

(Purification Step)
To the above filtrate, 0.05 g of phenothiazine and 0.05 g of 2,6-bis-t-butylhydroxytoluene were added, then the pressure was reduced to 0.7 kPa by a vacuum pump, and the solvent was distilled off. Subsequently, the pressure was reduced to 0.3 kPa, and distillation was carried out to obtain a distillate of 105 to 110° C. Thus, 26.2 g (0.11 mol) of 1,3-bisacryloyloxy-2-methyl-propane-2-isocyanate was obtained (yield: 58%).

Isocyanate Synthesis Example 2

Synthesis of 3-methacryloyloxyphenyl isocyanate (MPI)

(First Step)
In a 500 ml four-necked flask equipped with a stirrer, a thermometer, a dropping funnel and a reflux condenser, 30 g (0.275 mol) of 3-aminophenol (available from Mitsui Chemicals, Inc.) and 350 ml of 1,4-dioxane as a solvent were placed in a nitrogen atmosphere. Then, the solution was heated to 60° C., and a hydrogen chloride gas was fed at a flow rate of 100 ml/min for 1 hour and 10 minutes.

(Second Step)
The resulting solution was heated to 60° C., then 54.0 g (0.54 mol) of carbonyl chloride was fed over a period of 5 hours, and the temperature was maintained for 3 hours. After the reaction was completed, nitrogen was introduced to remove carbonyl chloride. A sample was withdrawn and analyzed by GC. As a result, 3-isocyanate phenol was obtained in a yield of 90%.

(Third Step)
To the resulting solution, 300 ml of o-dichlorobenzene was added, and 200 g (1.91 mol) of methacryloyl chloride and 1.0 g of phenothiazine were further added, followed by heating at 110° C. for 48 hours.

(Purification Step)

To the resulting reaction solution, 1.0 g of phenothiazine and 0.5 g of 2,6-bis-t-butylhydroxytoluene were added, then the pressure was reduced to 10 kPa by a vacuum pump, and the solvent was distilled off. The concentrated solution was placed in a 100 ml flask, then the pressure was reduced to 0.1 kPa, and distillation was carried out to obtain 13.8 g of a distillate of 123 to 125° C. The distillate was 3-methacryloyloxyphenyl isocyanate, and the yield was 25%.

Thiourethane Compound Synthesis Example 1

In a 100 ml egg plant type flask, 4.0 g (13.6 mmol) of BDMB, 20 g of toluene (available from Junsei Chemical Co., Ltd.) and 0.18 g (0.29 mmol) of dibutyltin dilaurate as a catalyst were placed, and a cooling tube was installed. With stirring the contents, 4.43 g (28.6 mmol) of 2-methacryloyloxyethyl isocyanate (MOI, available from Showa Denko K.K.) was dropwise added over a period of 30 minutes, followed by heating at an oil bath temperature of 50° C. After 5 hours, the reaction solution was allowed to cool, and an excess amount of 2-methacryloyloxyethyl isocyanate was removed by the use of hexane to obtain 7.22 g of a thiourethane compound BDMB-MOI (yield: 88%). A $^1$H-NMR spectrum of the resulting thiourethane compound BDMB-MOI is shown in FIG. 1.

Thiourethane Compound Synthesis Example 2

Figure 2:
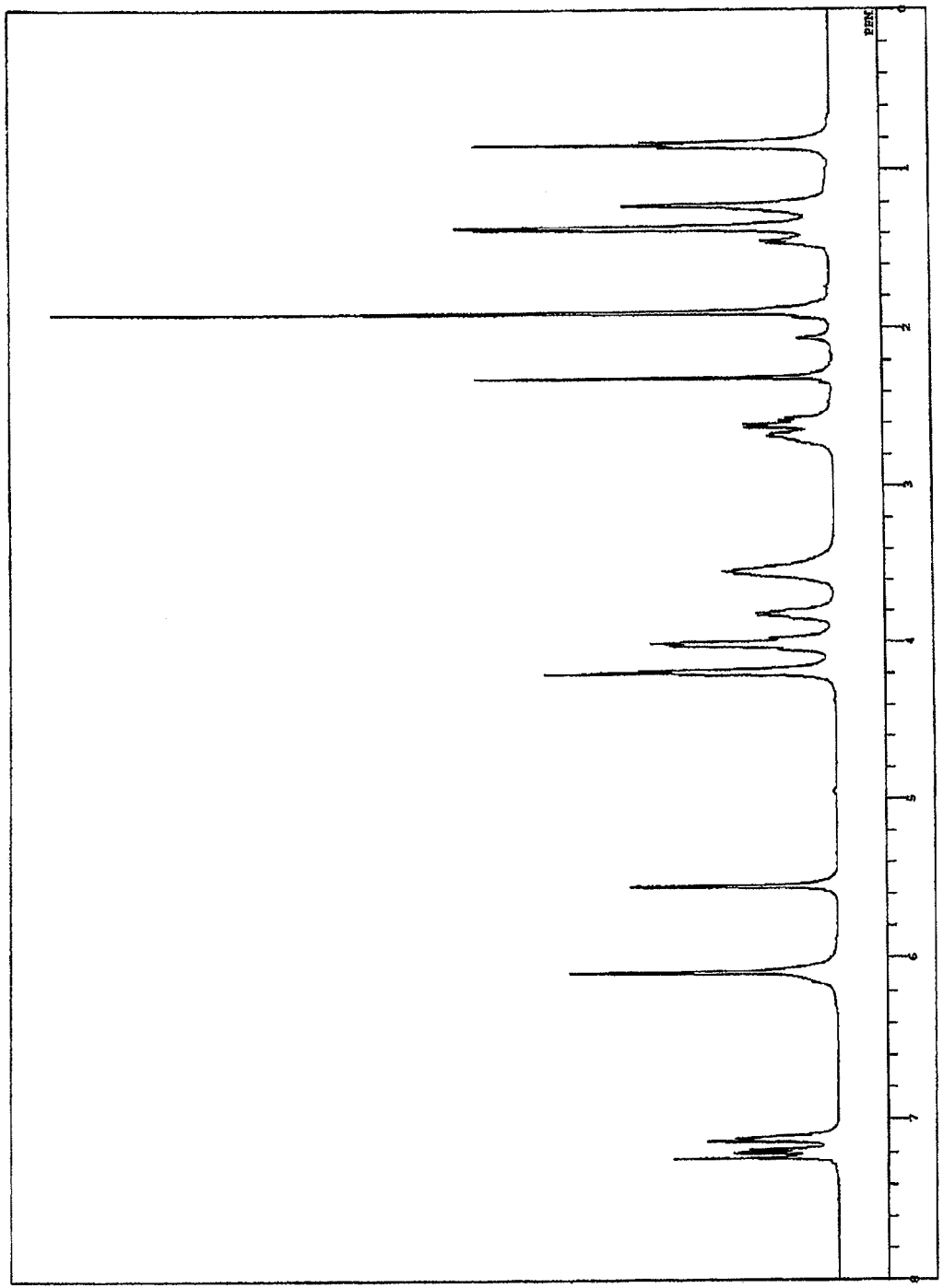
FIG. 2 is a graph of a $^1$H-NMR spectrum of a thiourethane compound TPMB-MOI synthesized in Thiourethane Compound Synthesis Example 2.

In a 100 ml egg plant type flask, 4.04 g (9.2 mmol) of TPMB, 20 g of toluene (available from Junsei Chemical Co., Ltd.) and 0.18 g (0.29 mmol) of dibutyltin dilaurate as a catalyst were placed, and a cooling tube was installed. With stirring the contents, 4.48 g (28.9 mmol) of 2-methacryloyloxyethyl isocyanate (available from Showa Denko K.K.) was dropwise added over a period of 30 minutes, followed by heating at an oil bath temperature of 50° C. After 5 hours from the initiation of reaction, the reaction solution was allowed to cool, and an excess amount of 2-methacryloyloxyethyl isocyanate was removed by the use of hexane to obtain 7.12 g of a thiourethane compound TPMB-MOI (yield: 85%). A $^1$H-NMR spectrum of the resulting thiourethane compound TPMB-MOI is shown in FIG. 2.

Thiourethane Compound Synthesis Example 3

Figure 3:
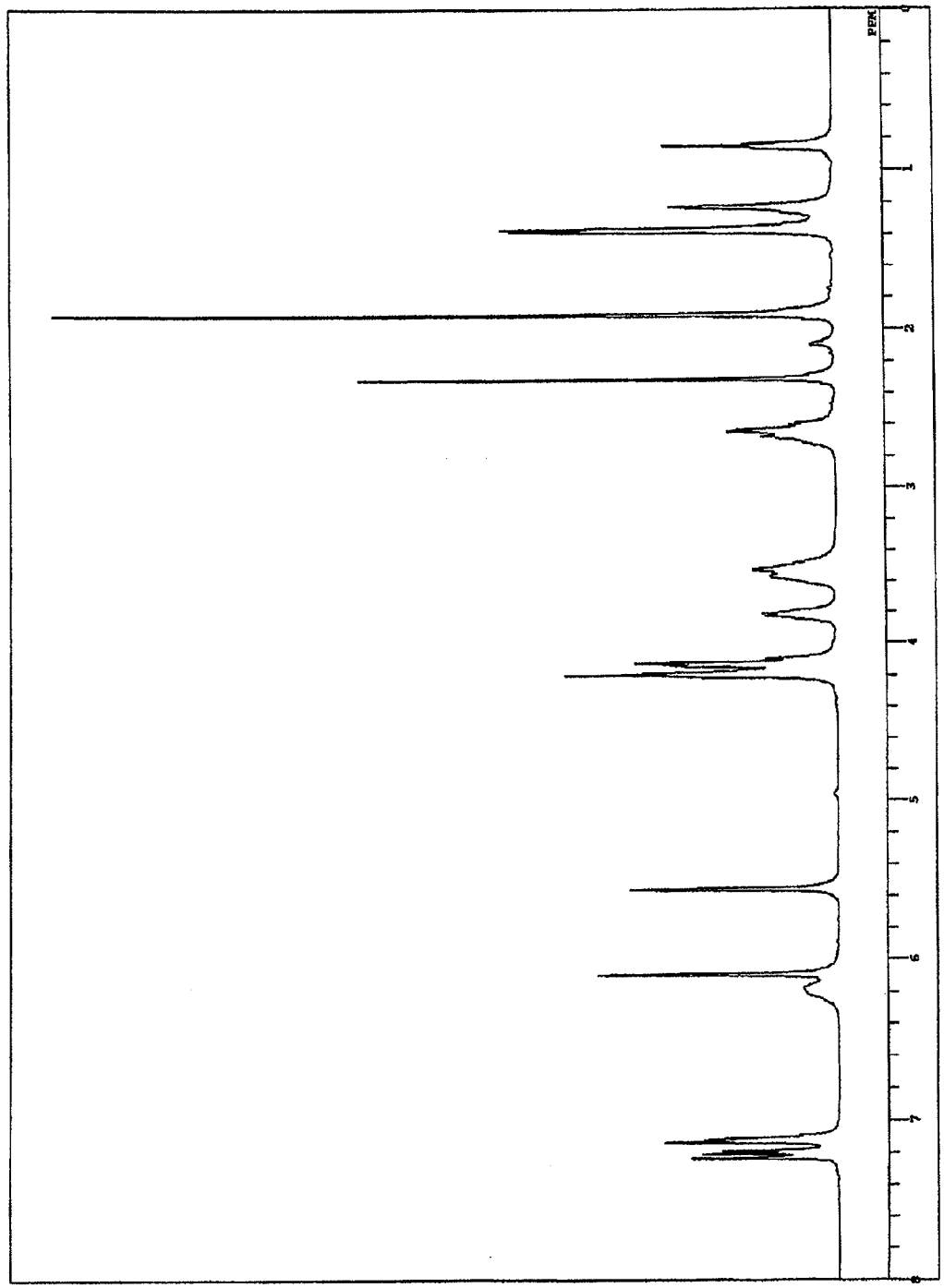
FIG. 3 is a graph of a $^1$H-NMR spectrum of a thiourethane compound PEMB-MOI synthesized in Thiourethane Compound Synthesis Example 3.

In a 100 ml egg plant type flask, 4.03 g (7.4 mmol) of PEMB, 20 g of toluene (available from Junsei Chemical Co., Ltd.) and 0.20 g (0.3 mmol) of dibutyltin dilaurate as a catalyst were placed, and a cooling tube was installed. With stirring the contents, 4.82 g (31.1 mmol) of 2-methacryloyloxyethyl isocyanate (available from Showa Denko K.K.) was dropwise added over a period of 30 minutes, followed by heating at an oil bath temperature of 50° C. After 6 hours from the initiation of reaction, the reaction solution was allowed to cool, and an excess amount of 2-methacryloyloxyethyl isocyanate was removed by the use of hexane to obtain 7.06 g of a thiourethane compound PEMB-MOI (yield: 82%). A $^1$H-NMR spectrum of the resulting thiourethane compound PEMB-MOI is shown in FIG. 3.

Thiourethane Compound Synthesis Example 4

Figure 4:
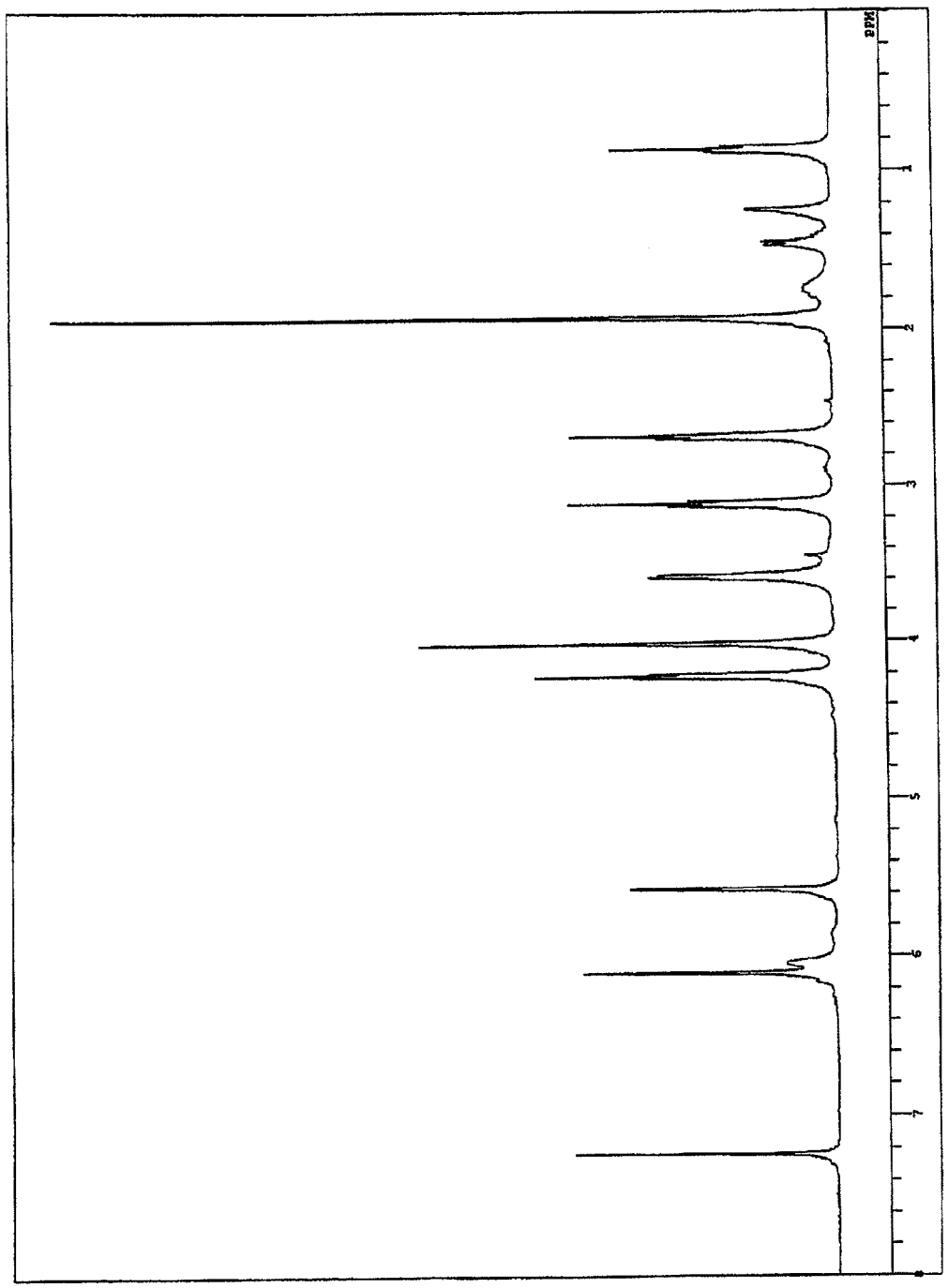
FIG. 4 is a graph of a $^1$H-NMR spectrum of a thiourethane compound TPMP-MOI synthesized in Thiourethane Compound Synthesis Example 4.

In a 100 ml egg plant type flask, 20 g (50.2 mmol) of trimethylolpropane tris(3-mercaptopropionate) (TPMP, available from Yodo Chemical Co., Ltd.) and 0.5 g (0.8 mmol) of dibutyltin dilaurate as a catalyst were placed, and a cooling tube was installed. With stirring the contents, 24.5 g (158 mmol) of 2-methacryloyloxyethyl isocyanate (available from Showa Denko K.K.) was dropwise added over a period of 120 minutes, and then stirring was continued at 28° C. for 4.5 hours. Then, excess amounts of 2-methacryloyloxyethyl isocyanate and TPMP were removed by the use of hexane to obtain 35.0 g of a thiourethane compound TPMP-MOI (yield: 81%). A $^1$H-NMR spectrum of the resulting thiourethane compound TPMP-MOI is shown in FIG. 4.

Thiourethane Compound Synthesis Example 5

Figure 5:
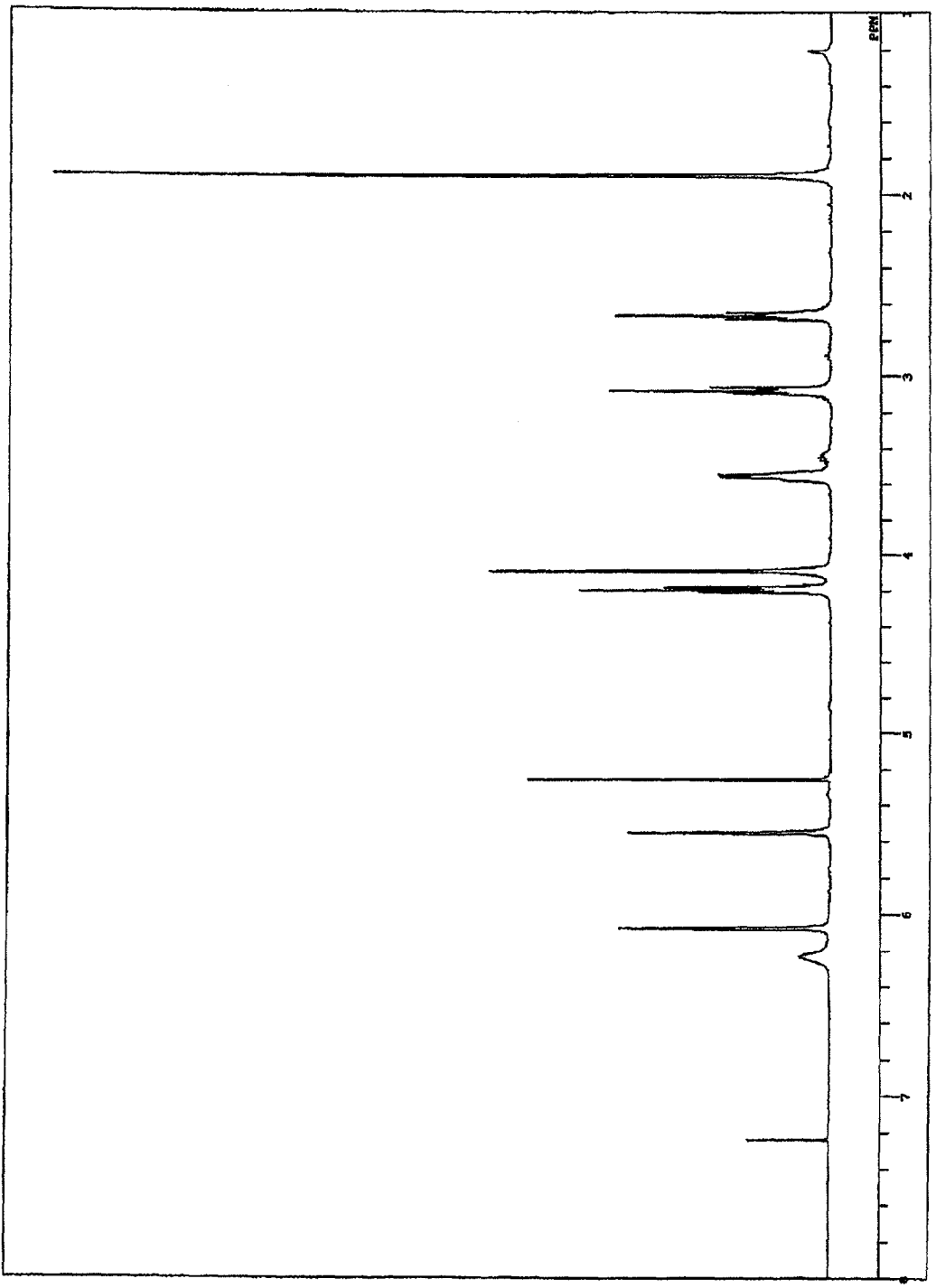
FIG. 5 is a graph of a $^1$H-NMR spectrum of a thiourethane compound PEMP-MOI synthesized in Thiourethane Compound Synthesis Example 5.

In a 100 ml egg plant type flask, 10 g (20.5 mmol) of pentaerythritol tetrakis(3-mercaptopropionate) (PEMP, available from Yodo Chemical Co., Ltd.) and 0.5 g (0.9 mmol) of dibutyltin dilaurate as a catalyst were placed, and a cooling tube was installed. With stirring the contents, 13.4 g (86.4 mmol) of 2-methacryloyloxyethyl isocyanate (available from Showa Denko K.K.) was dropwise added over a period of 60 minutes, and then stirring was continued at 35° C. for 7 hours. Then, excess amounts of 2-methacryloyloxyethyl isocyanate and PEMP were removed by the use of hexane to obtain 19.4 g of a thiourethane compound PEMP-MOI (yield: 86%). A $^1$H-NMR spectrum of the resulting thiourethane compound PEMP-MOI is shown in FIG. 5.

Thiourethane Compound Synthesis Example 6

Figure 6:
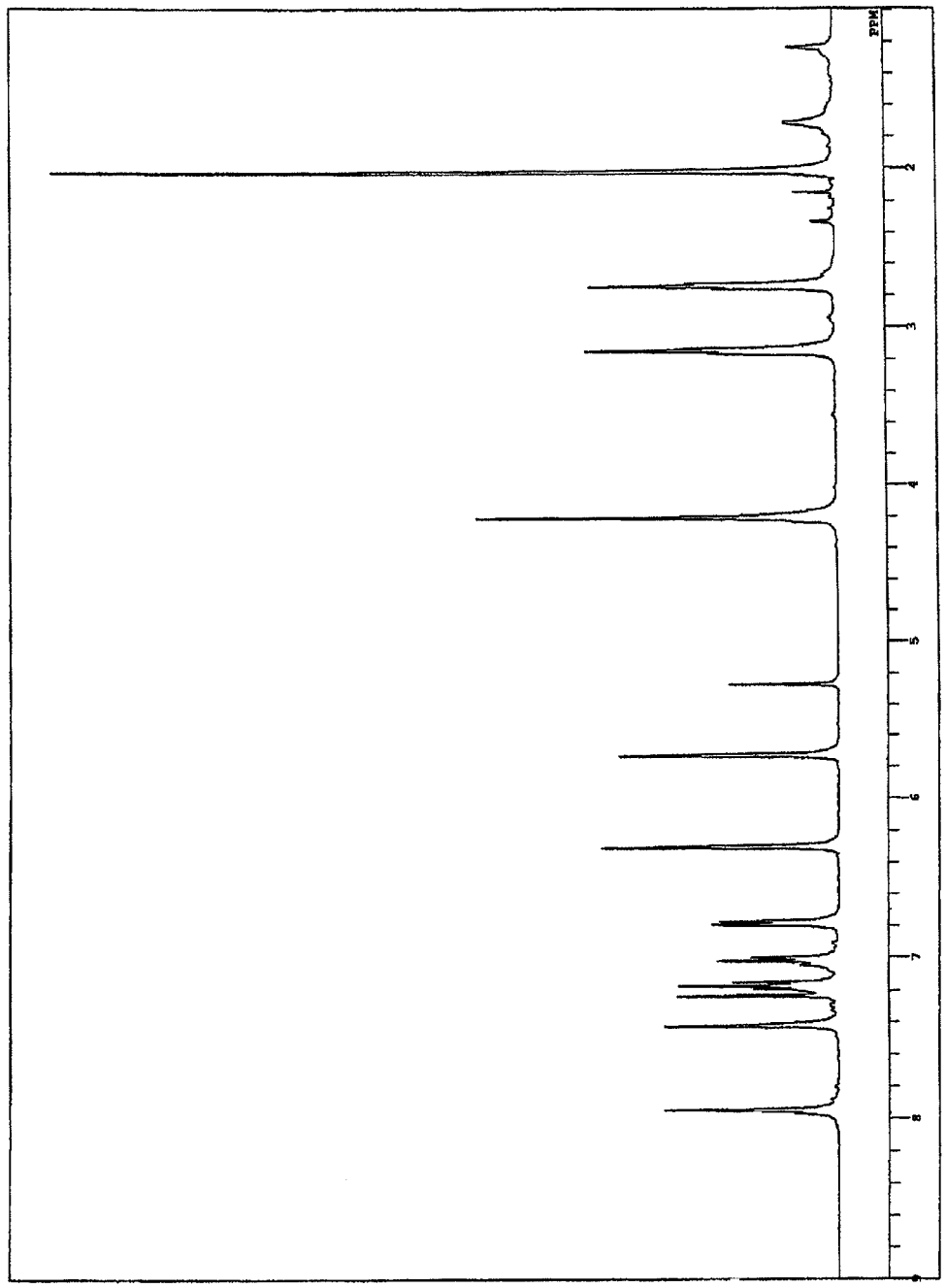
FIG. 6 is a graph of a $^1$H-NMR spectrum of a thiourethane compound PEMP-MPI synthesized in Thiourethane Compound Synthesis Example 6.

In a 100 ml egg plant type flask, 5.7 g (11.7 mmol) of pentaerythritol tetrakis(3-mercaptopropionate) (PEMP, available from Yodo Chemical Co., Ltd.), 10.0 g (49.3 mmol) of 3-methacryloyloxyphenyl isocyanate (MPI), 0.3 g (0.5 mmol) of dibutyltin dilaurate as a catalyst and 100 ml of methylene chloride as a solvent were placed, and a cooling tube was installed. The contents were stirred for 7.75 hours. After methylene chloride was distilled off, excess amounts of 3-methacryloyloxyphenyl isocyanate and PEMP were removed by the use of hexane to obtain 13.7 g of a thiourethane compound PEMP-MPI (yield: 90%). A $^1$H-NMR spectrum of the resulting thiourethane compound PEMP-MPI is shown in FIG. 6.

[Synthesis of Binder Resin (EP-1) Having Carboxyl Group on Side Chain]

185 g of Epicoat 1004 (bisphenol A type epoxy resin, available from Japan Epoxy Resins Co., Ltd., epoxy equivalent: 925), 14.4 g of acrylic acid, 0.20 g of hydroquinone and 197 g of diethylene glycol monomethyl ether acetate (abbreviated to "DGEA" hereinafter, available from Dicel Chemical Industries, Ltd.) were introduced, and they were heated to 95° C. After it was confirmed that the mixture had been homogeneously dissolved, 2.0 g of triphenylphosphine was introduced, and they were heated to 100° C. and allowed to undergo reaction for about 30 hours to obtain a reaction product having an acid value of 0.5 mgKOH/g. To the reaction product, 96.0 g of tetrahydrophthalic anhydride (available from New Japan Chemical Co., Ltd.) was added, and they were heated to 90° C. and allowed to undergo reaction for about 6 hours. Disappearance of absorption of the acid anhydride was confirmed by IR, and an epoxy acrylate resin EP-1 having a solid matter acid value of 119 mgKOH/g and a solids concentration of 60% was obtained.

[Preparation of Pigment Dispersion]

In a 300 ml stainless steel can, 1.98 g of Ajisper PB822 (pigment dispersant, available from Ajinomoto Fine-Techno Co., Inc.) was placed, and this was dissolved in 113.5 g of propylene glycol monomethyl ether acetate (abbreviated to "PMA" hereinafter, available from Dicel Chemical Industries, Ltd.). The resulting solution was mixed with 12.54 g of EP-1, 15.0 g of Special Black 350 (carbon black, available from Degssa Inc.) and 15.0 g of 13M-C (titanium black, available from Mitsubishi Material Corporation), and then 200 g of zirconia beads having a diameter of 0.65 mm were added, followed by carrying out dispersing treatment for 3 hours by the use of a paint conditioner (manufactured by Asada Iron Works Co., Ltd.). The resulting pigment dispersion was filtered through a filter paper having an opening diameter of 0.8 μm to give a black pigment dispersion.

[Preparation of Photosensitive Composition]

Photosensitive compositions of Examples 1 to 6 and Comparative Example 1 were prepared in blending ratios shown in Table 1.

TABLE 1

| Components of photosensitive composition | | | | Example 1 | | Example 2 | | Example 3 | | Example 4 | |
|---|---|---|---|---|---|---|---|---|---|---|---|
| | | | | Blending quantity (g) | Compositional ratio of solid matter (% by mass) | Blending quantity (g) | Compositional ratio of solid matter (% by mass) | Blending quantity (g) | Compositional ratio of solid matter (% by mass) | Blending quantity (g) | Compositional ratio of solid matter (% by mass) |
| Black pigment dispersion | | Whole | | 65.0 | 84.4 | 65.0 | 84.4 | 65.0 | 84.0 | 65.0 | 84.4 |
| | Constituents | Special Black 350 | *1 | (6.18) | (32.1) | (6.18) | (32.1) | (6.18) | (32.1) | (6.18) | (32.1) |
| | | 13M-C | *2 | (6.18) | (32.1) | (6.18) | (32.1) | (6.18) | (32.1) | (6.18) | (32.1) |
| | | Ajisper PB822 | *3 | (0.81) | (4.2) | (0.81) | (4.2) | (0.81) | (4.2) | (0.81) | (4.2) |
| | | EP-1 | | (3.09) | (16.0) | (3.09) | (16.0) | (3.09) | (16.0) | (3.09) | (16.0) |
| | | PMA | *4 | (46.68) | (—) | (46.68) | (—) | (46.68) | (—) | (46.68) | (—) |
| | | DGEA | *5 | (2.06) | (—) | (2.06) | (—) | (2.06) | (—) | (2.06) | (—) |
| Compound having ethylenically unsaturated bond | Light Acrylate BP-4EA | | *6 | 0.20 | 1.0 | 0.20 | 1.0 | 0.20 | 1.0 | 0.20 | 1.0 |
| | Aronix M-400 | | *7 | 0.50 | 2.6 | 0.50 | 2.6 | 0.50 | 2.6 | 0.50 | 2.6 |
| Component to constitute photopolymerization initiator composition | EMK | | *8 | 0.30 | 1.5 | 0.30 | 1.5 | 0.30 | 1.5 | 0.30 | 1.5 |
| | Irgacure 907 | | *9 | 1.00 | 5.2 | 1.00 | 5.2 | 1.00 | 5.2 | 1.00 | 5.2 |
| | Thiourethane compound | Quantity | | 1.00 | 5.2 | 1.00 | 5.2 | 1.00 | 5.2 | 1.00 | 5.2 |
| | | Type | | BDMB-MOI | | TPMB-MOI | | PEMB-MOI | | TPMP-MOI | |
| Organic solvent | Cyclohexanone | | | 31.98 | — | 31.98 | — | 31.98 | — | 31.98 | — |
| Leveling agent | Megafac R08 | | *10 | 0.02 | 0.1 | 0.02 | 0.1 | 0.02 | 0.1 | 0.02 | 0.1 |
| Total | | | | 100.0 | 100.0 | 100.0 | 100.0 | 100.0 | 100.0 | 100.0 | 100.0 |

| Components of photosensitive composition | | | | Example 5 | | Example 6 | | Comparative Example 1 | |
|---|---|---|---|---|---|---|---|---|---|
| | | | | Blending quantity (g) | Compositional ratio of solid matter (% by mass) | Blending quantity (g) | Compositional ratio of solid matter (% by mass) | Blending quantity (g) | Compositional ratio of solid matter (% by mass) |
| Black pigment dispersion | | Whole | | 65.0 | 84.4 | 65.0 | 84.4 | 65.0 | 88.9 |
| | Constituents | Special Black 350 | *1 | (6.18) | (32.1) | (6.18) | (32.1) | (6.18) | (33.8) |
| | | 13M-C | *2 | (6.18) | (32.1) | (6.18) | (32.1) | (6.18) | (33.8) |
| | | Ajisper PB822 | *3 | (0.81) | (4.2) | (0.81) | (4.2) | (0.81) | (4.4) |
| | | EP-1 | | (3.09) | (16.0) | (3.09) | (16.0) | (3.09) | (16.9) |
| | | PMA | *4 | (46.68) | (—) | (46.68) | (—) | (46.68) | (—) |
| | | DGEA | *5 | (2.06) | (—) | (2.06) | (—) | (2.06) | (—) |
| Compound having ethylenically unsaturated bond | Light Acrylate BP-4EA | | *6 | 0.20 | 1.0 | 0.20 | 1.0 | 0.20 | 1.1 |
| | Aronix M-400 | | *7 | 0.50 | 2.6 | 0.50 | 2.6 | 0.50 | 2.7 |
| Component to constitute photopolymerization initiator composition | EMK | | *8 | 0.30 | 1.5 | 0.30 | 1.5 | 0.30 | 1.6 |
| | Irgacure 907 | | *9 | 1.00 | 5.2 | 1.00 | 5.2 | 1.00 | 5.5 |
| | Thiourethane compound | Quantity | | 1.00 | 5.2 | 1.00 | 5.2 | — | — |
| | | Type | | PEMP-MOI | | PEMP-MPI | | — | |

TABLE 1-continued

| | | | | | | | | |
|---|---|---|---|---|---|---|---|---|
| Organic solvent | Cyclohexanone | | | 31.98 | — | 31.98 | — | 31.98 | — |
| Leveling agent | Megafac R08 | *10 | 0.02 | 0.1 | 0.02 | 0.1 | 0.02 | 0.1 |
| Total | | | 100.0 | 100.0 | 100.0 | 100.0 | 99.0 | 100.0 |

Notes of *1 to *10 in Table 1 are as follows.
*1: carbon black, available from Degssa Inc.
*2: titanium black, available from Mitsubishi Material Corporation
*3: pigment dispersant, available from Ajinomoto Fine-Techno Co., Inc.
*4: propylene glycol monomethyl ether acetate, available from Dicel Chemical Industries, Ltd.
*5: diethylene glycol monoethyl ether acetate, available from Dicel Chemical Industries, Ltd.
*6: bisphenol A EO 4 mol addition diacrylate, available from Kyoeisha Chemical Co., Ltd.
*7: dipentaerythritol hexaacrylate, available from Toagosei Co., Ltd.
*8: N,N-bis(diethylamino)benzophenone, available from Hodogaya Chemical Co., Ltd.
*9: 2-methyl-1-[4-(methylthio)phenyl]-2-morpholinopropan-1-one, available from Ciba Specialty Chemicals Inc.
*10: fluorine-based compound, available from Dainippon Ink & Chemicals Inc.

[Evaluation of Photosensitive Composition]

The photosensitive compositions of Examples 1 to 6 and Comparative Example 1 were each applied to a glass substrate (size: 100×100×1 mm) by spin coating so that the dry film thickness would become about 1 μm, then allowed to stand at room temperature for 30 minutes and thereafter dried at 70° C. for 20 minutes to remove the solvent, whereby resist films were formed. The thickness of each resist film was measured by a film thickness meter ("SURFCOM130A" manufactured by Tokyo Seimitsu Co., Ltd.), and then the resist film was cured by exposing the film to light through a quartz photomask by the use of an exposure device (manufactured by Ushio Inc., trade name: Multilight ML-251A/B) in which an extra-high pressure mercury lamp had been incorporated, with stepwise changing the quantity of exposure light automatically. The quantity of exposure light was measured by the use of an ultraviolet integration actinometer (manufactured by Ushio Inc., trade name: UIT-150, receptor: UVD-S365). The quartz photomask was a photomask on which a pattern having line/space of 5, 7, 10, 30, 50, 70 and 100 μm had been formed.

The resist film exposed to light as above was subjected to alkali development by an aqueous solution (25° C.) containing 0.25% of Developer 9033 (available from Shipley Far East Ltd.) that was an alkali developing agent containing potassium carbonate and 0.03% of sodium dodecylbenzenesulfonate, for a given period of time. The developing time was set to 2.0 times the time (tD) required for completely dissolving the coating film before the light exposure by the alkali development (in this example, tD was 25 seconds). After the alkali development, the resist film was washed with water, and the glass substrate was dried by air spraying. Then, the film thickness of the residual resist was measured, and a residual film ratio was calculated. The residual film ratio was calculated from the following formula.

Residual film ratio (%)=100×(film thickness after alkali development)/(film thickness before alkali development)

Further, the same photo-curing operation as above was carried out with changing the quantity of exposure light. Then, a graph in which a relationship between the quantity of exposure light and the residual film ratio was plotted was prepared, and a quantity of exposure light at which the residual film ratio reaches saturation was determined.

Furthermore, a line width of a resist having been formed by the photomask region having line/space of 10 μm was measured by a light microscope (VH-Z250, manufactured by Keyence Corporation).

A quantity of exposure light at which the residual film ratio after alkali development reaches saturation and the line width of the resist becomes the same as the line width of the photomask (10 μm) was determined by the above method, and the resulting quantity of exposure light was regarded as a photosensitivity. The results are set forth in Table 2.

TABLE 2

| | Photosensitivity (mJ/cm$^2$) |
|---|---|
| Example 1 | 75 |
| Example 2 | 25 |
| Example 3 | 50 |
| Example 4 | 75 |
| Example 5 | unevaluated |
| Example 6 | unevaluated |
| Comparative Example 1 | 150 |

The invention claimed is:

1. A thiourethane compound represented by the following formula (II):

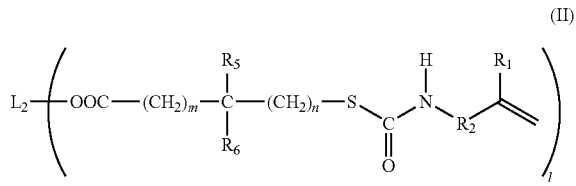

(II)

wherein $R_1$ is a hydrogen atom or a methyl group, $R_2$ is —CO—, —COO— or —COOR$_3$— (wherein $R_3$ is an alkylene group of 2 to 6 carbon atoms), $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent obtained from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate.

2. A thiourethane compound represented by the following formula (III):

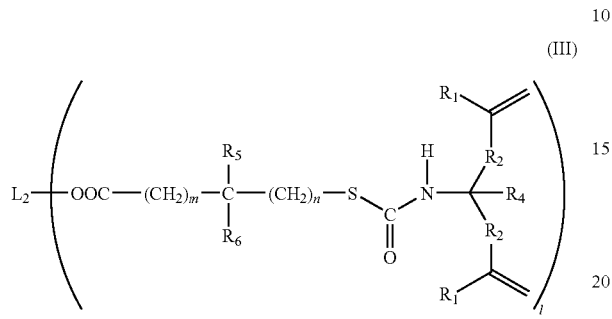

(III)

wherein $R_1$ is a hydrogen atom or a methyl group, $R_2$ is —CO—, —COO— or —COOR$_3$— (wherein $R_3$ is an alkylene group of 2 to 6 carbon atoms), $R_4$ is a hydrogen atom or a methyl group, $R_5$ and $R_6$ are each a hydrogen atom or an alkyl group of 1 to 10 carbon atoms, m is 0 or an integer of 1 to 2, n is 0 or 1, l is an integer of 2 to 6, and $L_2$ is a substituent obtained from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl) isocyanurate.

3. A thiourethane compound represented by the following formula (IV):

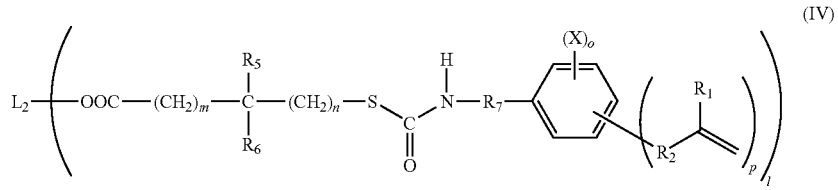

(IV)

wherein $R_1$ is a hydrogen atom or a methyl group, $R_2$ is —CO—, —COO— or —COOR$_3$— (wherein $R_3$ is an alkylene group of 2 to 6 carbon atoms), $R_5$ and $R_6$ are each a hydrogen atom or an alkyl group of 1 to 10 carbon atoms, $R_7$ is a direct bond or a straight-chain or branched alkylene group of 1 to 5 carbon atoms, m is 0 or an integer of 1 to 2, n is 0 or 1, l is an integer of 2 to 6, X is a hydrogen atom, a halogen atom or an electron attractive group, o is an integer of 0 to 4, p is an integer of 1 to 3, o and p satisfy the condition of $1 \leq o+p \leq 5$, and $L_2$ is a substituent obtained from a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris (2-hydroxyethyl)isocyanurate.

4. A process for preparing the thiourethane compound of claim 1 which is represented by the formula (II), comprising allowing
a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and
an ethylenically unsaturated group-containing isocyanate compound represented by the following formula (VI) to react with each other;

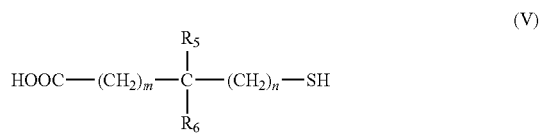

(V)

wherein $R_5$ and $R_6$ are each a hydrogen atom or an alkyl group of 1 to 10 carbon atoms, m is 0 or an integer of 1 to 2, and n is 0 or 1;

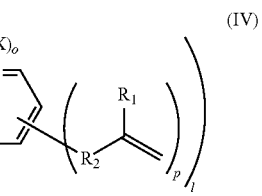

(VI)

wherein $R_1$ is a hydrogen atom or a methyl group, and $R_2$ is —CO—, —COO— or —COOR$_3$— (wherein $R_3$ is an alkylene group of 2 to 6 carbon atoms).

5. A process for preparing the thiourethane compound of claim 2 which is represented by the formula (III), comprising allowing
a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and an ethylenically unsaturated group-containing isocyanate compound represented by the following formula (VII) to react with each other;

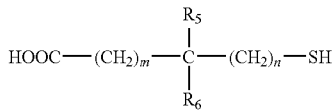
(V)

wherein $R_5$ and $R_6$ are each a hydrogen atom or an alkyl group of 1 to 10 carbon atoms, m is 0 or an integer of 1 to 2, and n is 0 or 1;

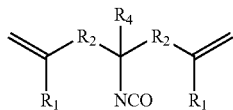
(VII)

wherein $R_1$ is a hydrogen atom or a methyl group, $R_2$ is —CO—, —COO— or —COOR$_3$— (wherein $R_3$ is an alkylene group of 2 to 6 carbon atoms), and $R_4$ is a hydrogen atom or a methyl group.

6. A process for preparing the thiourethane compound of claim 3 which is represented by the formula (IV), comprising allowing a thiol compound obtained by esterification reaction of a mercapto group-containing carboxylic acid compound represented by the following formula (V) with a polyfunctional alcohol compound selected from an alkylene glycol having an alkylene group of 2 to 10 carbon atoms which may be branched, diethylene glycol, dipropylene glycol, glycerol, trimethylolpropane, trimethylolethane, pentaerythritol, dipentaerythritol, cyclohexanediol, cyclohexanedimethanol, norbornenedimethanol, bisphenol A, hydrogenated bisphenol A, 4,4'-(9-fluorenylidene)bis(2-phenoxyethanol) and tris(2-hydroxyethyl)isocyanurate, and an ethylenically unsaturated group-containing isocyanate compound represented by the following formula (VIII) to react with each other;

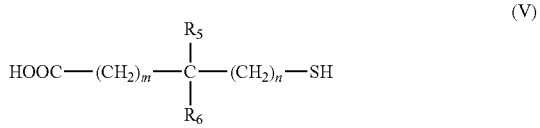
(V)

wherein $R_5$ and $R_6$ are each a hydrogen atom or an alkyl group of 1 to 10 carbon atoms, m is 0 or an integer of 1 to 2, and n is 0 or 1;

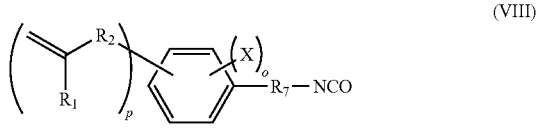
(VIII)

wherein $R_1$ is a hydrogen atom or a methyl group, $R_2$ is —CO—, —COO— or —COOR$_3$— (wherein $R_3$ is an alkylene group of 2 to 6 carbon atoms), $R_7$ is a direct bond or a straight-chain or branched alkylene group of 1 to 5 carbon atoms, X is a hydrogen atom, a halogen atom or an electron attractive group, o is an integer of 0 to 4, p is an integer of 1 to 3, and o and p satisfy the condition of $1 \leq o+p \leq 5$.

7. A photopolymerization initiator composition comprising the thiourethane compound of claim 1 and a photopolymerization initiator.

8. The photopolymerization initiator composition as claimed in claim 7, further comprising a sensitizer.

9. A photosensitive composition comprising the photopolymerization initiator composition of claim 7 and a compound having an ethylenically unsaturated bond.

10. The photosensitive composition as claimed in claim 9, further comprising a high-molecular polymer.

11. The photosensitive composition as claimed in claim 10, wherein the high-molecular polymer is a polymer soluble in a solvent or an alkali aqueous solution.

12. The photosensitive composition as claimed in claim 9, further comprising a pigment.

13. A color filter having a colored pattern comprising the photosensitive composition of claim 12 on a substrate.

* * * * *